US009713554B2

(12) United States Patent
Barda et al.

(10) Patent No.: US 9,713,554 B2
(45) Date of Patent: Jul. 25, 2017

(54) APPARATUS AND METHOD FOR ANALYSING EVENTS FROM SENSOR DATA BY OPTIMISATION

(71) Applicant: Fred Bergman Healthcare PTY LTD, North Sydney (AU)

(72) Inventors: David Albert Barda, Rose Bay (AU); Mohammad Hadi Mashinchi, Newtown (AU)

(73) Assignee: Fred Bergman Healthcare Pty. Ltd., North Sydney (AU)

( * ) Notice: Subject to any disclaimer, the term of this patent is extended or adjusted under 35 U.S.C. 154(b) by 0 days.

(21) Appl. No.: 14/925,443

(22) Filed: Oct. 28, 2015

(65) Prior Publication Data

US 2016/0158071 A1 Jun. 9, 2016

Related U.S. Application Data

(63) Continuation of application No. 13/704,153, filed as application No. PCT/AU2011/000727 on Jun. 16, 2011, now Pat. No. 9,224,102.

(Continued)

(51) Int. Cl.
*G06N 5/04* (2006.01)
*A61F 13/42* (2006.01)
(Continued)

(52) U.S. Cl.
CPC ............... *A61F 13/42* (2013.01); *G06N 5/04* (2013.01); *G06N 7/005* (2013.01); *G06N 99/005* (2013.01)

(58) Field of Classification Search
None
See application file for complete search history.

(56) References Cited

U.S. PATENT DOCUMENTS

2007/0270774 A1* 11/2007 Bergman ............... A61F 13/42
604/361

* cited by examiner

*Primary Examiner* — Alan Chen
(74) *Attorney, Agent, or Firm* — Hansen IP Law PLLC

(57) ABSTRACT

The present invention relates to sensor signal analysis. It relates particularly, but not exclusively, to methods, systems and devices for monitoring and processing the sensor signals to determine automatically characteristics of events represented by the sensor signals. The present invention is particularly, but not exclusively, related to methods, systems and devices for monitoring moisture in absorbent articles such as diapers, incontinence garments, dressings and pads resulting from wetness events caused by, for example, urinary and/or faecal incontinence. In an embodiment, the invention includes a method for processing sensor signals representing an event in an absorbent article. The method comprises: receiving sensor signals from a sensor representing one or more events in an absorbent article; and processing the sensor signals to determine a characteristic of at least one event in the absorbent article. One such characteristic can include the volume of a voiding event such as a urinary incontinence event. In another embodiment, the method includes carrying out a learning phase including the steps of: receiving sensor signals representing one or more events in each of one or more absorbent articles; receiving observation data indicative of a cumulative characteristic of the one or more events in each absorbent article; and identifying an optimal mathematical model describing a relationship between the sensor signals and the observation data. Such events can include urinary incontinence events occurring in absorbent articles such as diapers. Observation data can be measured cumulative volume of a cycle of voiding events occurring in a diaper.

24 Claims, 14 Drawing Sheets

Related U.S. Application Data

(60) Provisional application No. 61/437,018, filed on Jan. 28, 2011, provisional application No. 61/355,257, filed on Jun. 16, 2010.

(51) Int. Cl.
*G06N 99/00* (2010.01)
*G06N 7/00* (2006.01)

APPARATUS AND METHOD FOR ANALYSING EVENTS FROM SENSOR DATA BY OPTIMISATION

CROSS-REFERENCE TO RELATED APPLICATIONS

This application is a continuation of U.S. patent application Ser. No. 13/704,153, which is a national stage entry of Patent Cooperation Treaty Application No. AU/11/00727, filed on Jun. 16, 2011, which claims the benefit of U.S. Provisional Patent Application No. 61/355,257, filed on Jun. 16, 2010 and 61/437,018, filed on Jan. 28, 2011. Each of the foregoing applications is hereby incorporated by reference in its entirety.

FIELD OF THE INVENTION

The present invention relates to sensor signal analysis. It relates particularly, but not exclusively, to methods, systems and devices for monitoring and processing the sensor signals to determine automatically characteristics of events represented by the sensor signals. The present invention is particularly, but not exclusively, related to methods, systems and devices for monitoring moisture in absorbent articles such as diapers, incontinence garments, dressings and pads resulting from wetness events caused by, for example, urinary and/or faecal incontinence.

BACKGROUND OF THE INVENTION

Incontinence is a condition in which there is an uncontrolled release of discharges or evacuations. Urinary incontinence refers to loss of bladder control resulting in involuntary or uncontrolled urination. Other forms of incontinence include faecal or bowel incontinence.

There is a range of recognised forms of incontinence. Stress incontinence, also known as effort incontinence, refers to involuntary loss of continence associated with coughing, sneezing, lifting, straining or other physical exertion. Urge incontinence is involuntary loss of urine coupled with a strong desire to urinate. Overflow incontinence refers to involuntary loss of continence associated with a chronically distended and overfull bladder. Dribble incontinence refers to a leakage of urine without warning or provocation. Persons suffering from dribble incontinence often need to wear protective pads or diapers throughout the day and night. Functional incontinence refers to when a person recognises the need to urinate but cannot physically do so due to factors such as limited mobility.

Treatment options for incontinence can include behaviour management, medication and surgery. In circumstances where treatment is not available or unsuccessful the only option available is to address the incontinence events themselves. Such methods for addressing incontinence include the sufferer wearing an absorbent pad or diaper.

Because most sufferers of incontinence tend to be elderly or suffering from some form of disability a significant proportion of patients in care institutions such as hospitals, nursing homes, aged care facilities and geriatric institutions are sufferers of incontinence. Furthermore, a significant proportion of patients in care of such facilities suffer from incontinence on a regular basis.

To comply with regulations and protocols to ensure that the patients in care institutions are looked after it has been necessary for staff to conduct manual checks of patients suffering from incontinence on a regular basis. Such manual checks are typically carried out whether or not the patient has suffered an incontinence event as often the patient is unwilling or unable to alert staff of the fact that an incontinence event has occurred. As can be appreciated, the need to conduct regular checks of patients for incontinence is a significant drain on the resources of the patient care institutions and also causes interruption to a patient's rest and sleep.

Incontinence indicators and detection systems exist. However, existing continence detection systems are generally unable to distinguish a urinary incontinence event from a faecal incontinence event. Nor are existing incontinence detection systems able to detect or determine useful information about incontinence events such as the volume of an incontinence event. The existing systems are deficient in that they may alert a staff member or carer of the fact that a wetness event has occurred but provide no practically useful information as to the size of the wetness event or of the quantity of wetness contained in an incontinence pad or diaper as a result of a series of wetness events. As a result, a staff member or carer may waste time or resources by having to check a patient on a regular basis to determine the size of a wetness event or the quantity of wetness contained in an absorbent pad or diaper in order to determine whether the absorbent pad or diaper requires changing. Accordingly, although existing systems can provide an alert when a wetness event occurs, this does not necessarily reduce the regularity with which a staff member or carer must check the patient.

Attempts to refine existing systems or develop new systems which are able to detect the type of event or the volume have been frustrated by difficulties to create an adequate simulation of the field environment for validating the systems during development. As a result, such systems have failed once deployed in actual care scenarios.

Attempts to use data collected in the field to analyse whether wetness events are urinary or faecal events or to obtain other useful information about wetness events have been frustrated by the fact that once there has been manual checking, by removing the absorbent article from the wearer and weighing the absorbent article, the absorbent article cannot be reused. This means that once the absorbent article has been removed subsequent wetness events cannot occur in the same absorbent article and be checked each time a wetness events takes place. Even if an absorbent article is removed from a wearer after each wetness event and weighed it is difficult to tell whether the volume of the wetness event as measured in the absorbent article corresponds to the volume associated with a single wetness event or a sequence of events.

The present invention seeks to ameliorate some or all of the problems set out above with existing methods and systems and to improve the efficiency of monitoring and management of incontinence by providing more information about the characteristics of incontinence events than has hitherto been possible with existing incontinence detection systems. Particularly, the present invention aims to improve upon the prior art methods and systems by detecting the occurrence of each event in a sequence of events and determining the size or volume of each individual event in an absorbent article, without the need to remove the pad from the wearer.

The present invention also aims to provide a method and a platform for information to be gathered by sensors detecting factors other than wetness with the aim of deriving information related to those other factors enabling other judgments or diagnoses to be made about patients. Accordingly, the present invention aims to improve the efficiency in monitoring and management of disabilities and disorders other than incontinence.

SUMMARY OF THE INVENTION

In a first aspect, the invention provides a method for determining a wetness status of an absorbent article worn by a subject, the method comprising:
  receiving sensor signals from a sensor representing one or more wetness events occurring in an absorbent article;
  processing the sensor signals to determine a cumulative volume of the one or more wetness events; and
  determining which of one or more volume ranges contains the cumulative volume, wherein each one of the volume ranges represents a wetness status.

Preferably, the wetness status includes whether it is the correct time to change the absorbent article worn by the subject.

In embodiments, determining which of one or more volume ranges contains the cumulative volume, includes comparing the cumulative volume with:
  an upper threshold wetness volume capacity of the absorbent article; or
  a lower threshold wetness volume capacity of the absorbent article.

Preferably, the upper and lower thresholds are selected from the group including 0 ml-200 ml, 100 ml-300 ml, 200 ml-400 ml, 300 ml-500 ml, 400 ml-600 ml, 500 ml-700 ml and 600 ml-800 ml.

In one embodiment of the method, analysis is carried out on information derived from sensors incorporated in or applied to absorbent articles such as pads, diapers, adult incontinence garments or the like where the sensors detect wetness resulting from urinary and faecal incontinence events. In embodiments, the present invention may include receiving sensor signals from sensors for detecting other phenomena such as movement, orientation, location, sound, colour, smells, temperature, acidity and/or basicity (pH), biochemistry including enzymes, proteins, amino acids, carbohydrates, lipids, glucose and other analytes that may be of interest to individuals and medical practitioners for the purpose of monitoring, assessing and diagnosing disorders, disabilities and disease.

In embodiments, the method enables analysis of sensor signals received from absorbent articles to determine the occurrence of wetness events and cumulative volume of wetness events occurring in an absorbent pad. Another advantage of the method is that it facilitates processing the sensor signals to determine which of one or more volume ranges, such as a not correct time to change volume range or a correct time to change volume range, contains the cumulative volume to thereby determine the wetness status (i.e. not correct time to change or correct time to change) of the absorbent article.

In embodiments, the step of processing the sensor signals includes identifying automatically the sensor signals representative of each individual wetness event and, from the sensor signals representative of each individual wetness event:
  (i) generating a representative vector for that wetness event;
  (ii) allocating weightings to the representative vector to generate a weighted representative vector for that wetness event; and
  (iii) allocating a wetness event volume to the weighted representative vector for that event.

Allocating a wetness event volume to the weighted representative vector for that wetness event can include comparing the weighted representative vector with clusters of weighted representative vectors to determine which one or more of the clusters the weighted representative vector is most similar to and allocating a wetness event characteristic of the one or more clusters to the weighted representative vector for that wetness event, wherein the wetness event characteristic indicates wetness event volume for that wetness event.

The wetness event characteristic allocated to the weighted representative vector can be a weighted average of wetness event characteristics of more than one cluster according to a degree of similarity of the weighted representative vector to the one or more clusters.

One embodiment of the inventive method includes carrying out a learning phase, including the steps of:
  receiving sensor signals representing one or more wetness events in each of one or more absorbent articles;
  receiving observation data indicative of a cumulative characteristic of the one or more wetness events in each absorbent article; and
  identifying an optimal mathematical model describing a relationship between the sensor signals and the observation data.

In a preferred embodiment, the optimal mathematical model is found by an iterative process in which alternative mathematical models are determined by the method and solved until an optimal mathematical model is identified and may thereafter be employed in an assessment phase. Preferably, the iterative process continues until, for example, a stopping condition such as a maximum number of iterations, is reached. The optimal mathematical model is identified as the model that provides the lowest, or highest, solution error between a sum of characteristic values for individual wetness events in a sequence as calculated by the mathematical model and the observation data describing the cumulative value of wetness events in the same sequence. Accordingly, in a preferred embodiment, the observation data describes a cumulative characteristic of the plurality of wetness events occurring in the absorbent article. For example, in one embodiment, the cumulative characteristic may be the cumulative volume of a sequence of wetness events occurring in an absorbent article. The cumulative characteristic is determined by weighing the article when it has been removed from the wearer, where the weight of the article is indicative of the cumulative volume of wetness events occurring in the article during use.

Preferably, the mathematical model includes a system of linear equations describing the relationship between the sensor signals and the observation data.

In a further preferred embodiment, the method includes:
  (i) generating a representative vector for each individual wetness event, the representative vector being comprised of one or more elements;
  (ii) allocating weightings to the elements of the representative vector to generate a weighted representative vector; and
  (iii) allocating each of the weighted representative vectors to one or more of a plurality of clusters of weighted representative vectors according to their relative similarity; and
  (iv) allocating a wetness event volume to each of the clusters based on the optimal mathematical model obtained during the learning phase.

The mathematical model to be employed in the method can include one or more coefficients that are optimised to determine the optimal mathematical model, for example: a value for each weighting applicable to each of the elements of the representative vectors; a value (i.e. volume amount) applicable to each cluster of similar (clustered) weighted representative vectors; and a reference, or hypothetical, weighted representative vector or centre value for each cluster. Throughout the specification the terms "group", "cluster" and "event type" are used interchangeably to refer to groups or clusters of similar weighted representative vectors grouped or clustered according to their relative similarity.

By determining the optimal mathematical model during the learning phase it is possible using the inventive method to determine during an assessment phase, with a degree of confidence, from sensor signals received from sensors in absorbent pads a characteristic, such as void volume of exudate, associated with individual wetness events in a sequence of events occurring in an absorbent article while it is being worn. The characteristic associated with each wetness event can be determined without requiring observation data in the form of the measured weight of each absorbent pad after a wetness event or a sequence of wetness events has occurred in the absorbent article. By gathering and processing information obtained during the learning phase the method can be used to estimate the characteristics, such as a wetness event volume, from information obtained from sensors such as wetness sensors incorporated in absorbent articles being worn by an individual.

A preferred embodiment of the inventive method includes normalizing the elements of the representative vector with respect to a reference range and allocating the weightings to the normalized elements of the representative vector to generate a weighted normalized representative vector.

In one embodiment, the method includes categorizing the representative vectors of events according to order of occurrence (e.g. $1^{st}$, $2^{nd}$, $3^{rd}$ etc.) in a sequence of events in the absorbent article and allocating different weightings to elements of the representative vectors according to their category.

In another embodiment, the elements of the representative vector can include one or more values derived from the sensor signals. Preferably, the values derived from the sensor signals can include any one or more of the group including:
  duration of the wetness event,
  time to reach a maximum sensor signal value for the wetness event,
  average value of the sensor signal during an increase in the signal to a maximum for the wetness event,
  the maximum signal value for the wetness event,
  the time taken to reach a minimum signal value for the wetness event,
  average value of the sensor signal during a decrease in the signal to a minimum for the wetness event,
  the minimum signal value for the wetness event,
  the order of the wetness event in a sequence of wetness events,
  the similarity of a single sensor signal to one or a combination of other sensor signals occurring at the same time.

In an embodiment of the method, the characteristics allocated to each of the clusters includes wetness event information (e.g. a volume). In another embodiment of the method, the characteristics allocated to each of the clusters includes a reference representative vector and a wetness event volume.

In another embodiment of the method, an element of the representative vector includes event information for a previous event in a sequence of events occurring in the absorbent article. In yet another embodiment, an element of the representative vector can include a value representing information from any one or more of a group of information types including:
  demographic information;
  environmental information;
  the order of the wetness event in a sequence of wetness events for the absorbent article;

It is to be understood that environmental factors can have an influence on wetness event volumes for an individual suffering from incontinence. Such environmental factors can include the temperature and humidity of the surrounding climate, light levels and a range of other factors. Accordingly, the method can be configured to accommodate any one or more of these environmental factors as elements of the representative vector for each wetness event.

In another embodiment, the method further includes, for each of the weighted representative vectors, determining a degree of belief of belonging to one or more of the plurality of clusters.

In yet another embodiment, the method further includes training a fuzzy neural network with the weighted representative vectors and the degree of belief of belonging information determined for each of the weighted representative vectors. In a preferred form, training the fuzzy neural network includes the step of allocating information to each of the clusters including a wetness event volume and a series of values corresponding to the degrees of belief of belonging information determined for each of the representative vectors.

The trained fuzzy neural network can be used during the assessment phase to determine the degree of belief of belonging information for a weighted representative vector representing a wetness event in an absorbent article. Accordingly, in a preferred embodiment the method includes using the trained fuzzy neural network during an assessment phase to determine the degree of belief of belonging information for a weighted representative vector representing a wetness event in an absorbent article including determining the degree of belief of belonging to one or more of the plurality of clusters.

In another embodiment, the method further includes identifying weighted representative vectors that have less than a predetermined degree of confidence of belonging to any one of the clusters.

In a preferred form, the weighted representative vectors that are identified as having less than a predetermined degree of confidence of belonging to any one of the clusters are allocated to one or more clusters of representative vectors representing non-genuine wetness events.

In yet another embodiment, the method further includes verifying the correctness of the optimal mathematical model by receiving one or more sensor signals from a sensor representing a wetness event in an absorbent article, processing the sensor signals to determine a characteristic of the wetness event based on the optimal mathematical model obtained during the learning phase and comparing the determined characteristic with observation data.

In another embodiment, the step of identifying an optimal mathematical model includes determining a plurality of objective functions for evaluating the mathematical model and combining the objective functions according to a predetermined hierarchy of importance.

In embodiments the cumulative volume corresponds to a cumulative volume of wetness events in a pad resulting from a sequence of wetness events.

In embodiments, the method includes alerting a caregiver of the absorbent article wetness status.

In one embodiment, the step of identifying individual events from the sensor signals includes determining local maxima or minima of the sensor signals.

In another embodiment, the method includes smoothing the sensor signals received from the sensors.

In another aspect, the invention provides an incontinence monitoring system for determining a wetness status of an absorbent article worn by a subject, the system comprising:
an absorbent article including a sensor for sensing wetness events occurring in the absorbent article;
a processor for receiving sensor signals from the sensor representing one or more wetness events occurring in the absorbent article and processing the sensor signals to determine a cumulative volume of the one or more wetness events, determining which of one or more volume ranges contains the cumulative volume, wherein each one of the volume ranges represents a wetness status.

Preferably, the wetness status includes whether it is the correct time to change the absorbent article worn by the subject.

Determining which of one or more volume ranges contains the cumulative volume can include comparing the cumulative volume with:
an upper threshold wetness volume capacity of the absorbent article; or
a lower threshold wetness volume capacity of the absorbent article.

In embodiments, the processor sends information that is received by a caregiver's mobile device alerting the caregiver of the absorbent article wetness status.

BRIEF DESCRIPTION OF THE DRAWINGS

The present invention will now be described in greater detail with reference to the accompanying drawings. It is to be understood that the particularity of the accompanying drawings does not supersede the generality of the preceding description of the invention.

DETAILED DESCRIPTION

Figure 1A:
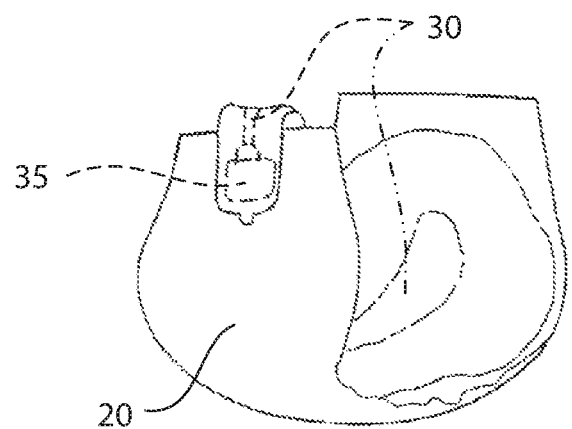
FIG. 1A illustrates a perspective view of an absorbent article component of a system for analyzing sensor signals representing a wetness event occurring in the absorbent article in accordance with an embodiment of the invention.

An embodiment of the present invention provides a method and a system for monitoring wetness in one or more absorbent articles such as pads, diapers, adult incontinence garments or the like. Throughout the description, reference will be made to a range of absorbent articles. It is to be understood that the list of absorbent articles above is not exhaustive and that other like garments are within the scope of the present invention.

The method of the present invention is generally intended for use in facilities in which monitoring and care of individuals with disabilities such as urinary and faecal incontinence take place. This may include facilities for the monitoring and care of the elderly or those suffering from some form of disability such as care institutions like hospitals, nursing homes, aged care facilities and geriatric institutions. However, it is envisaged that the present invention may be applicable in domestic or home monitoring of individuals, or in ambulatory monitoring.

Although the present invention is described herein with reference to a method of processing information derived from sensors incorporated in or applied to absorbent articles such as pads, diapers, adult incontinence garments or the like for detecting wetness resulting from urinary and faecal incontinence events it is to be appreciated that the present invention may have broader application. For example, the present invention may include detecting other phenomena such as temperature, acidity and/or basicity (pH), biochemistry including enzymes, proteins, amino acids, carbohydrates, lipids, glucose and other phenomena that may be of interest to individuals and medical practitioners for the purpose of monitoring, assessing and diagnosing disorders, disabilities and disease.

As well the urinary and faecal incontinence and wetness events referred to above, the present invention also has applicability in the detection, monitoring and management of conditions in which other fluids and exudates from the body may be present such as in wound management.

The present invention relates to a method for processing sensor signals representing an event in an environment, such as a wetness event in an absorbent article. The method comprises receiving from a sensor one or more sensor signals representing one or more events in an absorbent article. The sensor signals may be representative of an event or sequence of events, such as a voiding event, occurring in the absorbent article. The method also comprises processing the sensor signals to determine a characteristic of at least one event in the absorbent article. In a preferred form, processing the sensor signals includes identifying automatically the sensor signals representative of each individual event and, from the sensor signals representative of each individual event: (i) generating a representative vector for that event; (ii) allocating weightings to the representative vector to generate a weighted representative vector for that event; and (iii) allocating a characteristic to the weighted representative vector for that event. In a preferred form, the characteristic that is allocated to each weighted representative vector is a void event volume.

In the field of urinary and faecal incontinence it is useful to be able to derive information from sensors embedded in an absorbent article or pad which is additional to the mere occurrence of a wetness event. Embodiments of the method of the present invention are useful for determining information regarding the nature and volume of exudate associated with a wetness event and more particularly, the volume of individual events in a sequence of events occurring during the wearing of an absorbent pad. This information is useful to be able to determine the frequency, type and severity of each incontinence episode suffered by an individual and developing an incontinence profile in order to prescribe a suitable treatment or management plan for the individual's incontinence. It is also useful to determine when the total amount of exudate absorbed by an absorbent pad is approaching or has reached the limit of the pad's absorbent capacity and whether changing of the pad is required. An aspect of the inventive method enables a determination of whether an absorbent pad is likely to require changing without necessarily requiring manual periodic checking of the pad by staff in a care facility.

In a preferred form, the method further includes a step of carrying out a learning phase for optimising the accuracy of calculations subsequently made during assessment. The learning phase includes a step of receiving sensor signals representing one or more events in each of one or more absorbent articles. The learning phase of the method also includes receiving observation data indicative of a cumulative characteristic, for example cumulative volume, of the one or more events in each absorbent article. The learning phase of the method then involves using the sensor signal information and the observation data to determine one or more mathematical models each describing a relationship between the sensor signals and the observation data and identifying an optimal one of the mathematical models describing a relationship between the sensor signals and the observation data. In a preferred form, each one of the mathematical models includes a system of linear equations describing the relationship between the sensor signals and the observation data. Identifying an optimal one of the mathematical models may involve, for example, identifying optimal coefficients of the model.

In a preferred form, the method includes:
(i) generating a representative vector for each individual event, the representative vector being comprised of one or more elements;
(ii) allocating weightings to the elements of the representative vector to generate a weighted representative vector;
(iii) allocating the weighted representative vectors of a plurality of events to a plurality of clusters according to their relative similarity; and
(iv) allocating a characteristic to each of the clusters based on the optimal mathematical model obtained during the learning phase.

Figure 2:
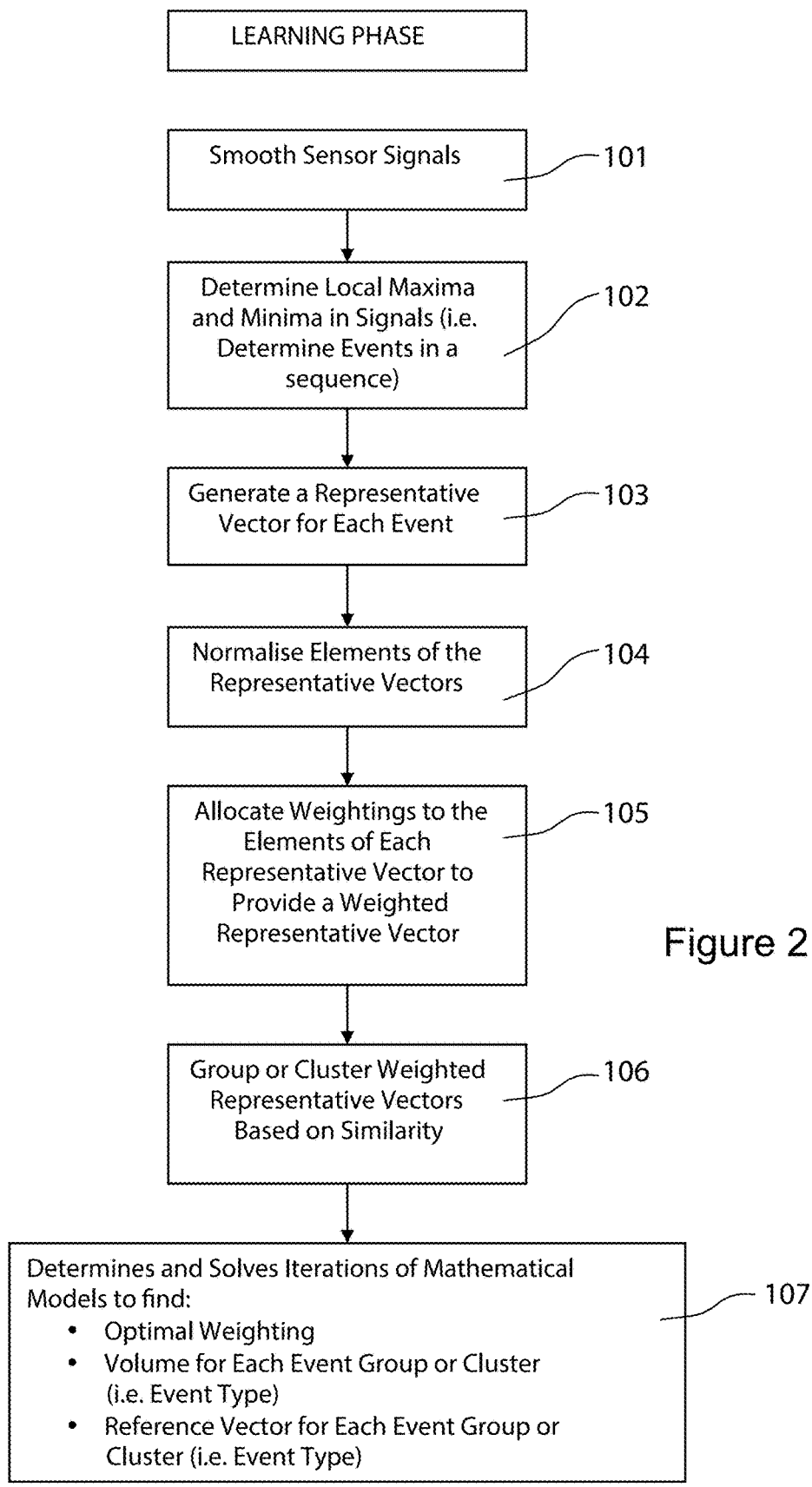
FIG. 2 is a flow diagram showing typical steps of a learning phase executed by the system in accordance with an embodiment of the invention.

Referring to FIG. 2, there is shown a flow chart illustrating an embodiment of the learning phase carried out in accordance with an embodiment of the method. In the learning phase sensor signals are received from sensors representing one or more events in each of one or more of the absorbent articles. The sensor signals typically include raw data associated with wetness events detected by the sensors in the absorbent articles.

The sensor signals are pre-processed in a manner that is described in more detail below. Pre-processing of the sensor signals includes smoothing 101 the sensor signals, determining local maxima and minima in the signals 102, generating a representative vector for each event 103 in a sequence of events represented by the sensor signals and normalising the sensor signals 104. The representative vector for each event 103 includes a number of elements which are values derived from the sensor signals. These include any one or more of the group including: duration of the event; time to reach a maximum sensor signal value for the event; average value of the sensor signal during an increase in the signal to a maximum for the event; the maximum signal value for the event; the time taken to reach a minimum signal value for the event; average value of the sensor signal during a decrease in the signal to a minimum for the event; the minimum signal value for the event; the order of the event in a sequence of events; or the similarity of a single sensor signal to one or a combination of other sensor signals occurring at the same time. Elements of the representative vector 103 can also include values representing information from any one or more of a group of information types including: demographic information; environmental information; and the order of the event in a sequence of events for the absorbent article.

The learning phase of the method also includes receiving observation data describing a characteristic of the events. Such observation data includes the time the observation was made and a measured cumulative weight of exudate contained within an absorbent article removed from an individual after changing, and whether the exudate contains urine, faecal matter of a combination of urine and faecal matter. The observation data may be manually or otherwise collected during the learning phase.

Elements of the representative vector are allocated random weightings to provide weighted representative vectors 105. This is because, as will be described in more detail below, it is not known at this stage how important any particular element of the mathematical model is to the characteristic of the event that is to be determined (i.e. the volume amount for an event). The weighted representative vectors are then grouped or clustered based on their relative similarity 106 in a manner that will be described in more detail below. The method then involves determining and finding solutions for one or more mathematical models 107 that describe a relationship between the sensor signals received from sensors embedded in one or more absorbent articles and cumulative observation data, namely the total weight of exudate, contained within each absorbent article monitored during the learning phase.

As will be described in more detail below with reference to FIG. 3 the method involves finding an optimal mathematical model, by iteratively generating and solving mathematical equations describing a relationship between the sensor signals and the observation data, until an optimal mathematical model is arrived at where the solution to the mathematical equations produces an optimal value such as a minimal error. In each iteration of the mathematical model components of the model such as the weightings given to each of the elements of the representative vector are altered. Each of the mathematical models is assessed and the accuracy of the mathematical model is evaluated by reference to an objective function, for example solution error. If an iteration of the mathematical model provides a relatively low solution error then the mathematical model is recorded. Further iterations of the mathematical model are generated until a stopping condition is reached, such as a user defined maximum number of iterations or when an acceptably low solution error is achieved. When the stopping condition is reached the optimal mathematical model, for example the mathematical model that provides the lowest solution error, is recalled to be utilised during the assessment phase.

During the learning phase, the optimal mathematical model includes event information for each of one or more event types. The event information can be determined according to a reference vector having a corresponding volume amount for each of the event types. The plurality of event types and the reference vector and the volume amount for each event type is determined during the learning phase by determining a reference vector for each event in a sequence of events for each absorbent article. The reference vector for each event is made up of the same elements as the representative vector, such as those derived from the sensor signals for each event, and for each different event, a representative vector is generated. Secondly, the method involves intuitively allocating the random weightings to each element of each of the representative vectors to provide weighted representative vectors. In one form, the method employs a strategy (such as genetic, tabu, simulated annealing, etc) to intuitively allocate random weightings to each element of each of the representative vectors to provide weighted representative vectors. The weightings, which at this stage are intuitively allocated and are yet to be optimised, represent the importance that each element in the representative vector has in determining the characteristic, for example volume, of the event.

In a preferred form, the method involves grouping, or clustering, similar weighted representative vectors according to their relative similarity while maximising the relative dissimilarity of the centres of the groups or clusters. Any number of groups or clusters may be adopted in the method. In the present embodiment, a category or set of groups or clusters is allocated to events based on the order of events in a sequence occurring in the absorbent articles (i.e. $1^{st}$, $2^{nd}$, $3^{rd}$ etc.). Thus, a first category of groups/clusters is allocated to the first of the events in a sequence of events in a number of absorbent articles, a second category of groups/clusters is allocated to the second of the events in the sequence of events in the absorbent articles and so on. Each category of groups/clusters may include two, three, or more groups or clusters. Each group or cluster has its own reference, or hypothetical, weighted representative vector. Thus, the weighted representative vector for the first event of a sequence of events in an absorbent article is allocated to a cluster according to which of the first event clusters the weighted representative vector is most similar to. Also, the weighted representative vector for the second event of the sequence of events in an absorbent article is allocated to a cluster according to which of the second event clusters the weighted representative vector is most similar to and so on. The same occurs for all of the remaining events in the sequence of events until all of the representative vectors for all of the events of the sequence are allocated to a group/cluster. Furthermore, during the learning phase, each group/cluster is associated with a characteristic value which is in turn associated with each of the weighted representative vectors that are grouped into that group/cluster. In preferred forms of the invention, the group/cluster value represents the volume amount for a voiding event. The volume amount values for each group/cluster are calculated in each iteration of the learning phase and comprise elements of the mathematical model representing the solution for that iteration. Once a stopping condition is reached, the iteration of the optimal mathematical model, which is the mathematical model which resulted in providing the optimal value according to the objective function, for example lowest solution error, is recalled and the characteristic values for each cluster from that optimal mathematical model are associated with each group/cluster for use in the assessment phase.

In a preferred embodiment, the weighted representative vectors are clustered according to a degree of belief of the similarity of each representative vector to one or more of a plurality of groups or clusters. This process, referred to as "fuzzy clustering", involves allocating a weighted representative vector obtained during either the learning phase or during the assessment phase to one, or more than one, "fuzzy" cluster with an accompanying degree of belief indicating the extent to which the weighted representative vector belongs to each of the one or more fuzzy clusters. In this embodiment, coefficients of degree of belief of belonging to the one or more of the fuzzy clusters are allocated to the weighted representative vectors. The degree of belief of belonging coefficients of the weighted representative vectors are a function of the similarity of the representative vectors to one or more groups or fuzzy clusters. The group or fuzzy cluster values for a weighted representative vector may be a weighted average of more than one group or fuzzy cluster value based on the degree of similarity or closeness of the representative vector to the centre of one or more groups or fuzzy clusters of representative vectors. Thus, for example, the degree of belief of belonging of a weighted representative vector to fuzzy cluster $x_1$ may be 0.2, to fuzzy cluster $x_2$ may be 0.5 and to fuzzy cluster $x_3$ may be 0.3 wherein the sum of the coefficients is 1.0. Thus, the coefficients of degree of belief allocated to the weighted representative vector will be 0.2 $x_1$, 0.5 $x_2$ and 0.3 $x_3$.

The optimization process carried out in the learning phase of the method is an iterative process in which iterations of the mathematical model determined by the method and describing a relationship between the sensor signals and the observation data are determined and solved and improved. Iterations of the mathematical model are determined and solved until a stop point is reached, such as a user defined number of iterations, and an optimal mathematical model is identified that involves, for example the lowest solution error. As a result of identifying the optimal mathematical model an optimal set of weightings for the elements of the representative vector to be employed by the method during the assessment phase are found. Also as a result of identifying the optimal mathematical model an optimal set of characteristic values for the clusters, such as the volume amount value for each cluster, are found. In embodiments of the method of the invention the mathematical model determined by the method is a system of linear equations describing the relationship between the sensor signals and the observation data. The linear equations preferably include a linear equation for each sequence of events for each absorbent article monitored during the learning phase. For example, if 200 absorbent pads are employed during the learning phase and each absorbent pad provides sensor data relating to one sequence of events then, during the learning phase, the method will involve determining mathematical models including at least 200 linear equations. Each linear equation relates the weighted representative vectors for each event in the sequence for each absorbent article and the cluster or fuzzy cluster values allocated to the weighted representative vectors by reference to their cluster, or fuzzy cluster, allocation with the observation data obtained for each absorbent article. In the present embodiment the observation data is the total or cumulative weight of exudate in the absorbent article resulting from a sequence of void events occurring in the absorbent article.

Figure 3:
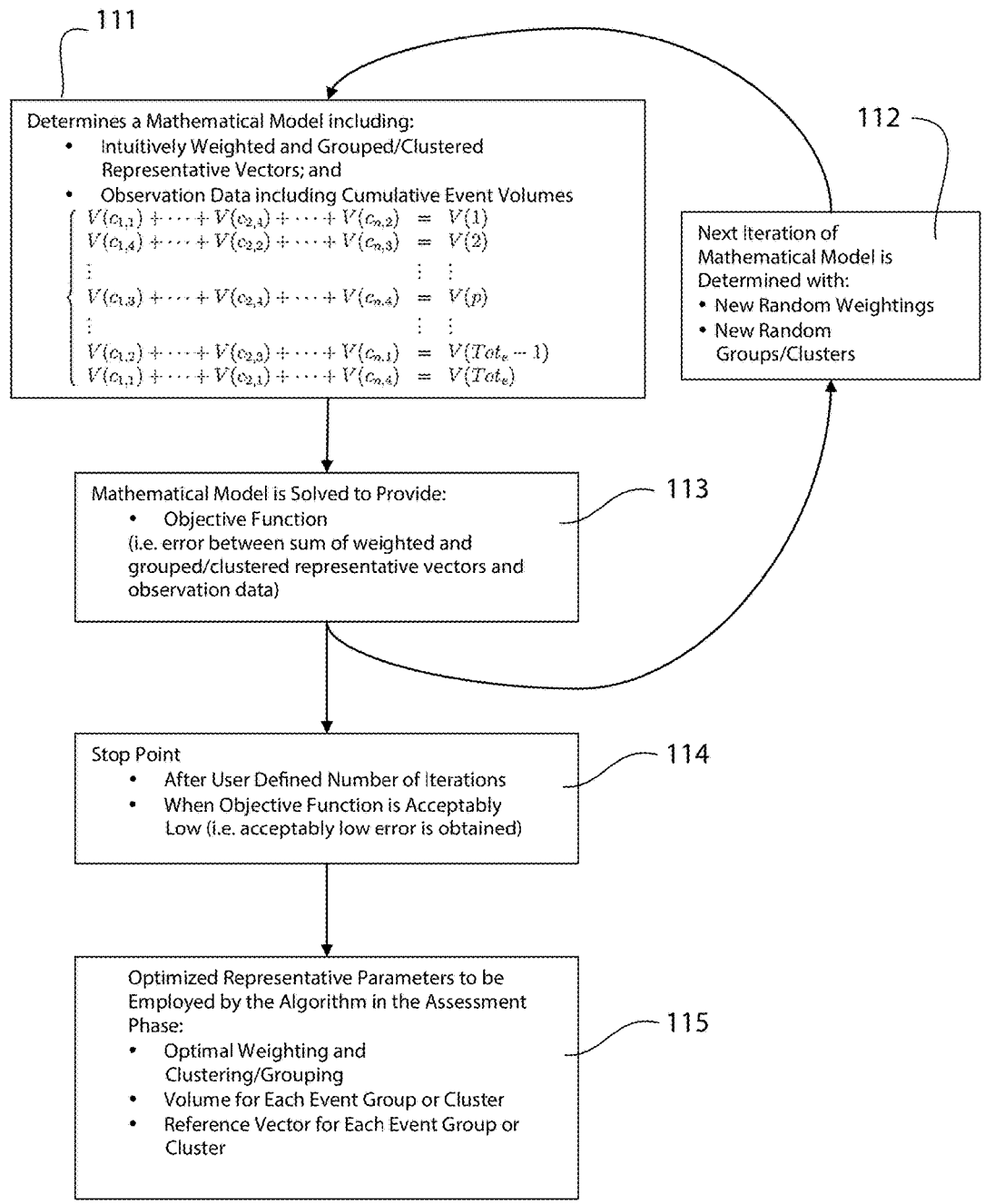
FIG. 3 is a flow diagram illustrating an optimisation process for a learning phase in which optimised parameters are determined for use during an assessment phase according to an embodiment of the invention.

Referring to FIG. 3, there is shown a flow chart illustrating how optimisation may be achieved according to the inventive method during the learning phase. In particular, the flow chart illustrates how the method determines and finds solutions for one or more mathematical models 111 each describing a relationship between the sensor signals and the observation data. Each of the mathematical models relates randomly weighted and clustered, or fuzzy clustered, representative vectors to the observation data indicating the cumulative volume of wetness events in a sequence of events. The mathematical model evolves through a number of iterations (step 112) in which the weightings and clustering, or fuzzy clustering, of the representative vectors are changed.

Each iteration of the mathematical model is solved at 113 to provide, for each model, the solution error between the sum of the event volumes determined according to the weighted and clustered representative vectors of each event in a sequence, and the measured cumulative volume of the events in the sequence occurring in the absorbent pad (observed volume). A number of iterations of the mathematical model are performed 112 until a stop point or stop condition 114 is reached. A stop point may be defined by e.g. a user defined number of iterations. The iteration of the mathematical model that produces, for example a lowest solution error, as evaluated by an objective function is considered to be the optimal mathematical model. This provides optimized parameters of the mathematical model at 115 which may then be employed in an assessment phase. The optimised parameters typically include:
  i) an optimal value for each weighting coefficient;
  ii) a value (i.e. volume amount) for each group or cluster; and
  iii) a reference, or hypothetical, weighted representative vector for each group or cluster (i.e. the centre of each group or cluster).

The information in items (i), (ii) and (iii) above identified during the learning phase are the optimized parameters employed in an assessment phase which is described in detail below.

Figure 4:
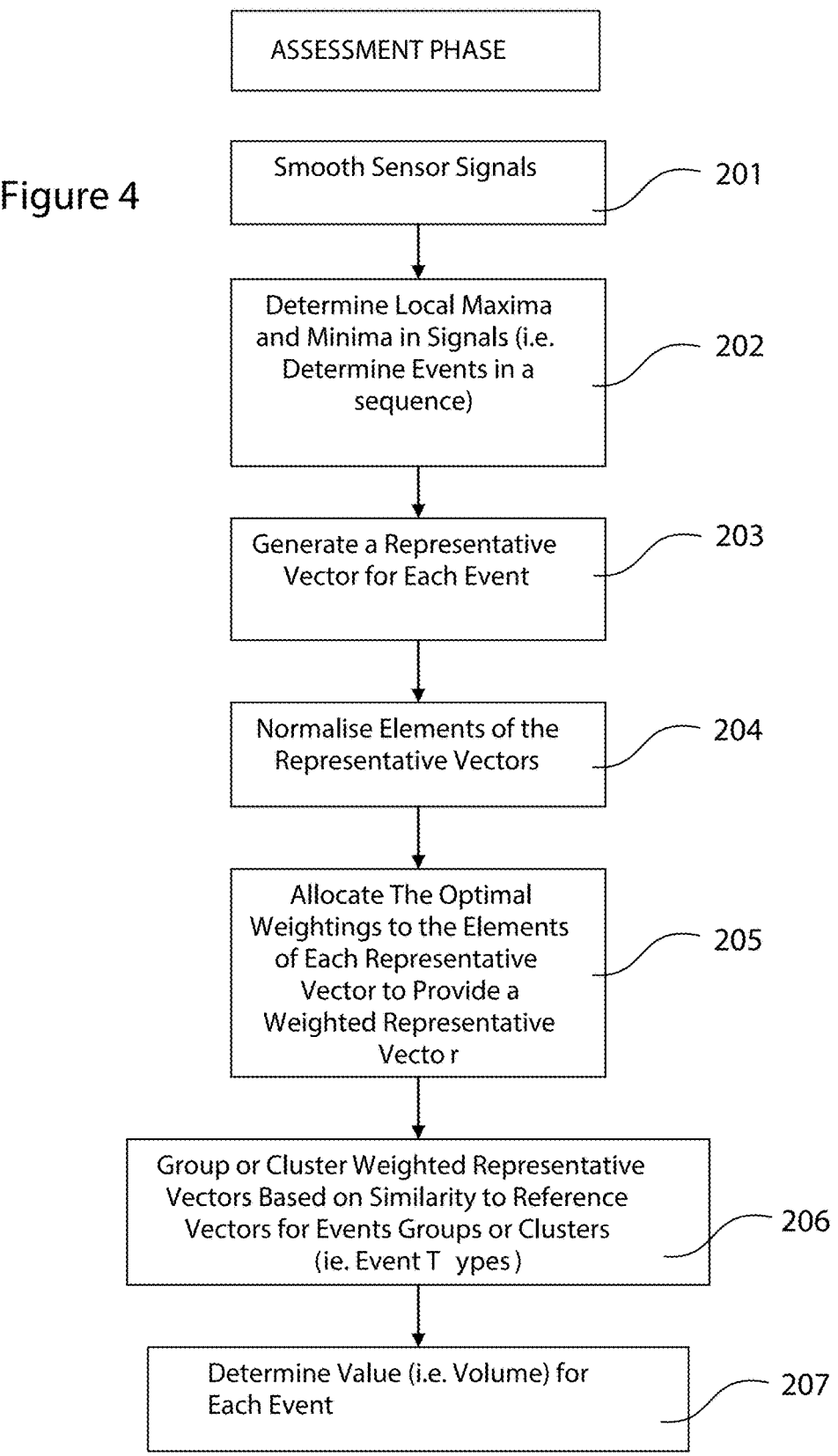
FIG. 4 is a flow diagram showing typical steps of an assessment phase executed by the system in accordance with an embodiment of the invention.

In FIG. 4 there is shown a flow chart illustrating steps in a method of assessing incontinence events in an absorbent article. The assessment phase employs optimised models obtained during the learning phase illustrated in FIGS. 2 and 3 and described above. In particular, the flow chart of FIG. 4 illustrates how, in the assessment phase, it is no longer necessary to receive observation data such as the total weight of exudate contained within each absorbent article after changing in order to ascertain the cumulative or event volume of wetness in the article. During the assessment phase, by using the optimised mathematical model obtained during the learning phase, the volume of exudate associated with each wetness event is estimated from sensor signals from sensors embedded in absorbent articles. Thus, there is no need to disrupt individuals wearing the absorbent articles to manually inspect their wetness condition.

The assessment method involves receiving sensor signals from the sensors embedded in the absorbent articles. The sensor signals are pre-processed in a manner that is described in more detail below. Pre-processing of the sensor signals includes smoothing 201 the sensors signals, determining local maxima and minima in the signals 202 to determine events in a sequence of events, generating a representative vector for each event 203 in a sequence of events represented by the sensor signals and normalising the sensor signals 204.

Using the optimised mathematical model obtained during the learning phase described above and illustrated in FIGS. 2 and 3, weightings are allocated to the elements of each representative vector to provide a weighted representative vector 205. The weighted representative vector calculated at 205 is then compared in a step 206 with the hypothetical, weighted representative vectors for each group or cluster (i.e. the centre of each group or cluster) where the clusters represent an event type. Clusters determined during the learning phase are employed during the assessment phase, to determine which group or cluster (i.e. event type) the weighted representative vector is most similar to. The method then involves allocating the value (i.e. volume amount) obtained during the learning phase for the relevant group or cluster (i.e. event type) to the event represented by the weighted and grouped/clustered representative vector thus providing an estimated volume of exudate associated with the event in a step 207.

Where the method involves fuzzy clustering, the weighted representative vectors obtained during the assessment phase are allocated degree of belief coefficients according to a degree of belief of the similarity of the weighted representative vectors to one or more groups or fuzzy clusters of weighted representative vectors determined during the learning phase. Thus, the weighted representative vector for an event may have allocated to it a weighted average of values (i.e. volume amount) of more than one fuzzy cluster based on the degree of similarity or closeness of the representative vector to the reference vectors (i.e. the centres) of the fuzzy clusters. Thus, a voiding event volume estimate for an individual voiding event may be determined by the method during the assessment phase to be a weighted average of the volumes of a plurality of fuzzy clusters allocated to the fuzzy clusters during the learning phase.

Figure 1B:
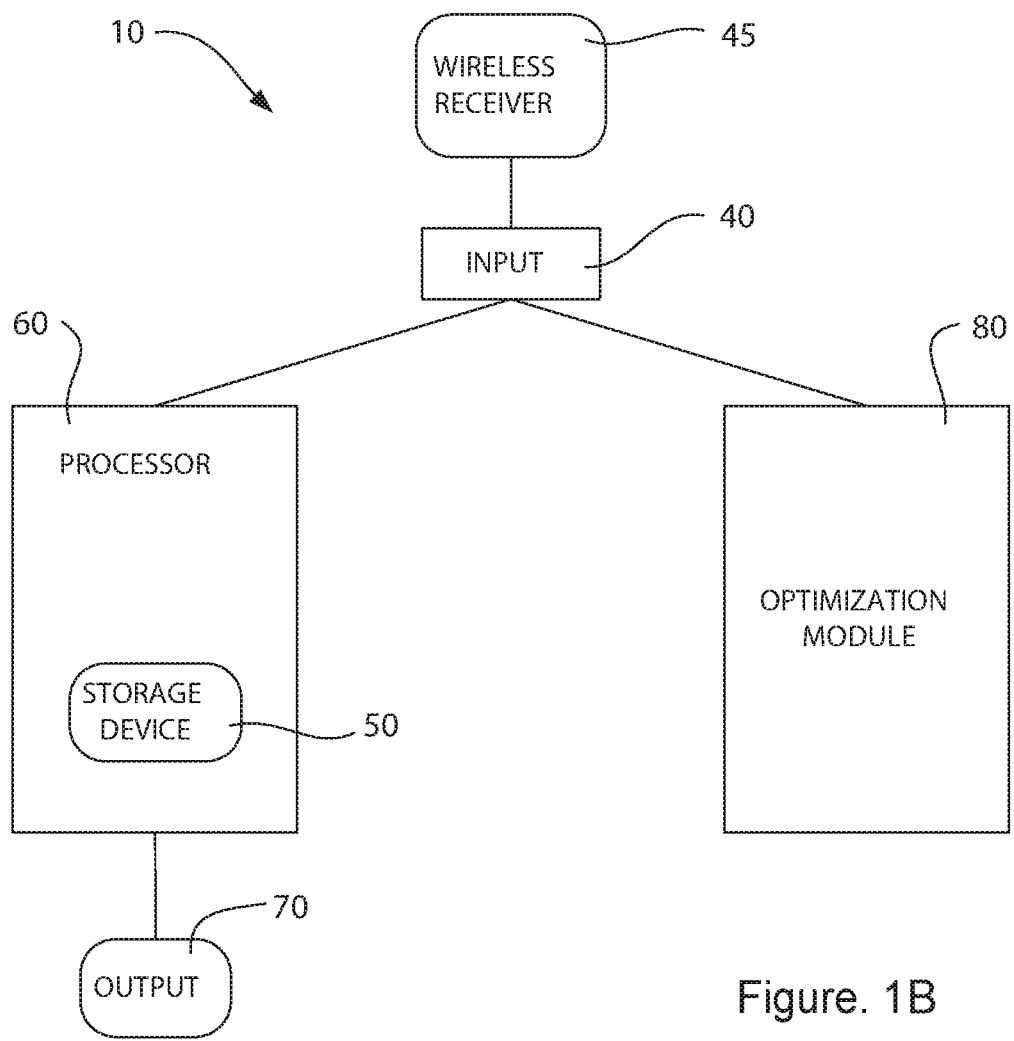
FIG. 1B is a schematic diagram illustrating features of a system for analysing for analyzing sensor signals representing a wetness event occurring in an absorbent article in accordance with an embodiment of the invention.

Referring now to FIG. 1B, there is shown a schematic diagram illustrating features of a system 10 for implementing the method of the invention. The system 10 is adapted for analysing sensor signals representing an event in an environment such as an absorbent article 20. The system 10 includes an input 40 for receiving one or more sensor signals representing one or more events in the absorbent article 20. The system 10 also includes a storage device 50, a processor 60 and an output 70. An algorithm is stored on the storage device 50 as a set of instructions executed by the processor 60 to carry out a method for processing the sensor signals to determine a characteristic of at least one event in the absorbent article 20. The output 70 communicates the characteristic of the at least one event with a user of a system 10 e.g. via a display device such as a computer monitor.

In one embodiment, the system 10 is configured to receive sensor signals from a plurality of sensors 30 embedded in the absorbent article 20. The sensors 30 are adapted to detect the presence of moisture which is indicated by an increase in conductivity between spaced electrodes as a result of moisture forming a conductive bridge between the electrodes. However, the sensors 30 could be replaced or complimented with sensors for detecting other phenomena such as temperature, acidity and/or basicity (pH), biochemistry including enzymes, proteins, amino acids, carbohydrates, lipids, glucose and other phenomena that may be of interest to individuals and medical practitioners for the purpose of monitoring, assessing and diagnosing disorders, disabilities and disease.

In a clinical environment such as in a hospital, and aged care facility or the like the system 10 may include a wireless signal transmission device 35 that is coupled to the sensors 30 embedded in the absorbent article 20 using a physical connector or contactless coupling. The transmission device 35 is adapted to wirelessly transmit sensor signals that are received by a wireless receiver device 45 connected to the input 40. Thus, the signals generated by the sensors 30 in the absorbent article 20 can be transmitted wirelessly to the input 40 such that a hard line between the sensors 30 and the input 40 of the system 10 is not required.

The algorithm is executed by the processor 60 to perform an analysis of the sensor signals to characterise wetness events occurring in the absorbent articles being monitored. In one embodiment, the analysis involves carrying out a method of the invention by applying a mathematical model describing a relationship between sensor signals representing a sequence of events and a characteristic of the event such as a cumulative volume of exudate associated with wetness in the absorbent article. The mathematical model may be determined or optimised by processor 60 or by a separate processor or processing means.

The system 10 illustrated in FIG. 1 also includes an optimization module 80. The optimization module 80 carries out a learning phase of an embodiment of the invention. The optimisation module 80 executes the learning phase for optimizing one or more parameters employed by the algorithm. The optimization module 80 performs an analysis of the sensor signals received by the input 40 to characterise wetness events occurring in the absorbent articles being monitored during the learning phase. It is to be noted, however that the optimization module need not be provided as part of the analysis system deployed into care institutions. Although that may be the case, it is also contemplated that the optimization module may be provided separately and remotely from the analysis elements of the system, e.g. at sites where observation data is readily available for use in the learning phase executed by the optimization module.

In a preferred form, the system 10 involves grouping, or clustering, similar weighted representative vectors according to their relative similarity while maximising the relative dissimilarity of the centres of the groups or clusters. The system 10 clusters weighted representative vectors according to a degree of belief of the similarity of each representative vector to one or more groups or clusters. This process, referred to as fuzzy clustering, involves allocating a weighted representative vector obtained during either the learning phase or during the assessment phase to more than one fuzzy cluster with a degree of belief of belonging of the weighted representative vector to each of the fuzzy clusters.

In an embodiment, the invention involves capturing the knowledge obtained by the fuzzy clustering process carried out during a learning phase and applying it during an assessment phase. One preferred form, capturing the knowledge of the fuzzy clustering process carried out during the learning phase involves training a fuzzy neural network. Thus, in one embodiment, the system 10 includes a fuzzy neural network in the form of an algorithm that may be executed by the optimisation module 80 and/or the processor 60. The optimisation module 80 and/or the processor 60 executes the fuzzy neural network algorithm to capture the knowledge of the fuzzy clustering process described above. As mentioned above, during the learning or optimization phase, when the fuzzy clustering occurs, each weighted representative vector representing an event is categorised in one or more of the fuzzy clusters with a degree of belief of belonging to the one or more fuzzy clusters. The degree of belief is typically represented by degree of belief coefficients. The information that is obtained from the fuzzy clustering process carried out during the learning phase can be used to train the fuzzy neural network such that during the assessment phase the trained fuzzy neural network can approximate the degree of belief of belonging of a given weighted representative vector derived from sensor signals representative of a detected event, to one or more of the clusters and thereby more accurately approximate a characteristic of the event. The fuzzy neural network is trained using input information and output information. In an embodiment, the fuzzy neural network is trained using the information obtained during the fuzzy clustering process. That is the weighted representative vector information for each of the events included in the learning phase, namely the input, and the degree of belief coefficients for each of these weighted representative vectors representing the degree of belief of belonging of the weighted representative vector to each of the fuzzy clusters, namely the output.

In an embodiment of the system, the processor 60 and the optimization module 80 identify in each of the signals one or more different void events. By identifying different void events from the signals representative of the void events the processor 60 and the optimization module 80 distinguish between different occasions on which exudate is passed by the wearer of the absorbent article 20. The processor 60 and the optimization module 80 then generate a representative vector for the signals representing each event for each absorbent article 20. The representative vector may be made up of a number of elements. Such elements may include the magnitude or strength of signals from one or more different sensors 30 embedded in the absorbent article 20. Other elements may include secondary values derived from the signals from the different sensors or other related observations, actions, demographic variable or environmental conditions. Some of the elements of the representative vector may be more indicative of a characteristic that a user wishes to know about an event than others. Accordingly, the elements of the representative vector are weighted according to a weighting vector to provide a weighted representative vector. This emphasises the effect of some factors and diminishes the influence of other factors when analysing the sensor signals.

The elements of the representative vectors for the events that are employed during the learning phase and the assessment phase are those that are considered likely to be representative of the characteristic of the event that is to be determined during the assessment phase. In these embodiments of the method and the system, the elements of the representative vectors for the events that are being monitored are those that are considered likely to be representative of the void volumes (or other characteristics being assessed) associated with incontinence events occurring in an absorbent article. The elements of the representative vectors derived from the sensor signals can include any one or more of the group including but not limited to:

duration of the event,
  time to reach a maximum sensor signal value for the event,
  average value of the sensor signal during an increase in the signal to a maximum for the event,
  the maximum signal value for the event,
  the time taken to reach a minimum signal value for the event,
  average value of the sensor signal during a decrease in the signal to a minimum for the event,
  the minimum signal value for the event,
  the position of the event in a sequence of events,
  the similarity of a single sensor signal to one or a combination of other sensor signals occurring at the same time.

The above elements of the representative vector are determined from the signals received from sensors in the method and from the sensors 30 by the input 40 in the system. However, it is also possible to receive other information in the method and to provide other information to the input 40 in the system relating to other elements that are not dependent on, or determined by, sensors signals received from sensors in an absorbent article in the method or from the sensors 30 in the absorbent article 20 in the system. Other such information could relate to elements of the representative vector that are user defined and include user defined values. One such user defined value could include a value representing the order of the event in a sequence of events, that is, whether an event is first, second, third, and so on, in a sequence of events that occur in the absorbent article. This information is considered to be relevant to the characteristic of the event that is to be determined, namely void volume of a wetness event, because the number of void events which may have occurred prior to the wetness event in question may impact on the sensor signals generated by the sensors 30 in the absorbent article 20 for subsequent events. For example, the sensor signals representative of a first event may be disproportionately lower or higher in magnitude in comparison to sensors signals representative of a second event, and lower or higher still than a third event, and so on, because residual wetness may remain in the absorbent article. This may sensitise or desensitise the sensors to subsequent wetness events.

Other information that may be received in the method or provided to the input 40 in the system relating to elements that are not dependant on, or determined by, sensor signals received from sensors in an absorbent article can include a value representing information from any one or more of a group of information types including demographic information of a wearer of the absorbent article; event sequence number information; elapsed time since the absorbent pad was changed; the time of day; ambient temperature; or the time since the patient last ingested food or liquid.

The relative importance of the elements of the representative vector derived from other information described above that is not derived from the sensor signals is determined by the method during the learning phase by determining the optimal weighting coefficients for the elements.

In embodiments of the method and the system, the processor 60 and the optimization module 80 normalize the elements of the representative vector with respect to a reference range to provide a normalized representative vector and allocate a weighting to the normalized elements of the representative vector to generate a weighted normalized representative vector. In order to make a comparison between the values of the different elements, whether that be sensor signal value, secondary information derived from sensor signals or values of other user defined elements, the values must be normalised by being converted into values falling within a common range, such as a value from 0 to 1. Ideally, normalisation of elements of representative vectors occurs during the learning phase and the assessment phase.

In further embodiments of the method and the system, the method, the processor 60 and the optimization module 80 process the sensor signals during the learning phase and during the assessment phase to identify in each of the signals one or more individual events. The derivative of each point of each sensor signal data gives the trend of the signal. The genuine events are detected by finding the local maxima of the signal. In a differentiable function, critical points represent either local minima or maxima. To rule out the local minima, as they do not represent the genuine events, and any local maxima that are not representative of genuine events the trends before and after the critical points are studied. In the sensor signals received in the method, and received by the input 20 from the sensors 30 in an absorbent article 20 in the system, the beginning of a wetness event occurring in the absorbent article is represented as a positive derivative of the sensor signal. The end of the wetness event occurring in the absorbent article is represented when the derivative of the signal is close to zero (theoretically zero). The beginning of the next wetness event in a sequence of events for the absorbent article is represented as the next occasion on which the sensor signal has a positive derivative. To put it another way, the method, the processor 60 and the optimization module 80 identify individual events in a sequence of events by determining local maxima or minima of the sensor signals. Accordingly, the method, the processor 60 and the optimization module 80 are capable of distinguishing between consecutive events occurring in each absorbent article during the learning phase and the assessment phase and can thereby determine the elements of the representative vector for use in the algorithm.

In order to enhance the ability of the method and processor 60 and the optimization module 80 of the system to determine local maxima and minima of the sensor signals received from sensors in each absorbent article the method and the processor 60 and the optimization module 80 of the system smooth the sensor signals such as by executing a smoothing algorithm. The smoothing algorithm may employ a smoothing coefficient that is either user defined or is optimised by an optimisation process. The optimal smoothing coefficient is one which enables the method and the processor 60 and the optimization module 80 of the system to determine local maxima and minima of signals received from sensors in absorbent articles that accurately correlate with the beginning and end of wetness events occurring in the absorbent article. The smoothing of the sensor signals and the determination of local maxima and minima form part of the pre-processing of the sensor signals in the learning and assessment phases illustrated in FIGS. 2 and 4.

An example of a preferred implementation of the invention including the Learning Phase and the Assessment Phase is set out below:

Smoothing the Sensor Signals

Figure 5:
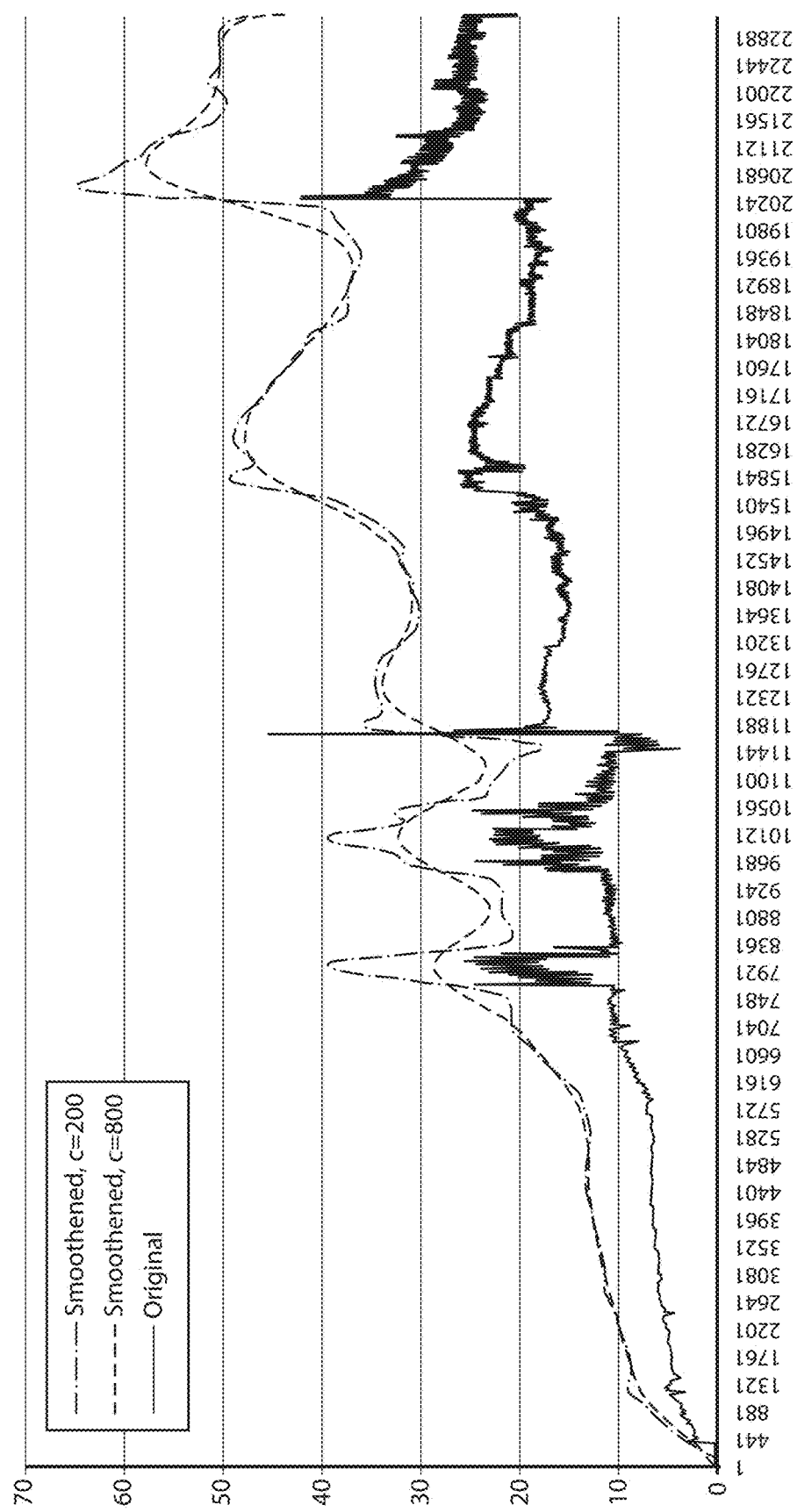
FIG. 5 is a graph illustrating an example of an original signal and its smoothened signals using two different smoothing coefficients in accordance with an embodiment of the invention

There are two main reasons that the sensors' data should be smoothed. First, to reduce the noise and consequently capture the important pattern of the signal and secondly to make the signal differentiable. The signal must be differentiable for the event detection phase. A user defined or optimisable variable (called smoothing coefficient) controls the extent of smoothing. The smoothing coefficient can be derived by a separate optimisation process in which the goal is to maximise the number of legitimate detected events in the event detection phase. FIG. 5 shows a graph illustrating an original signal and its smoothened signals with two different smoothing coefficients. The process of smoothing the sensor signal may also involve interpolation of missing data resulting from an interruption of the sensor signal or because of some other reason.

Genuine Event Detection

Figure 6:
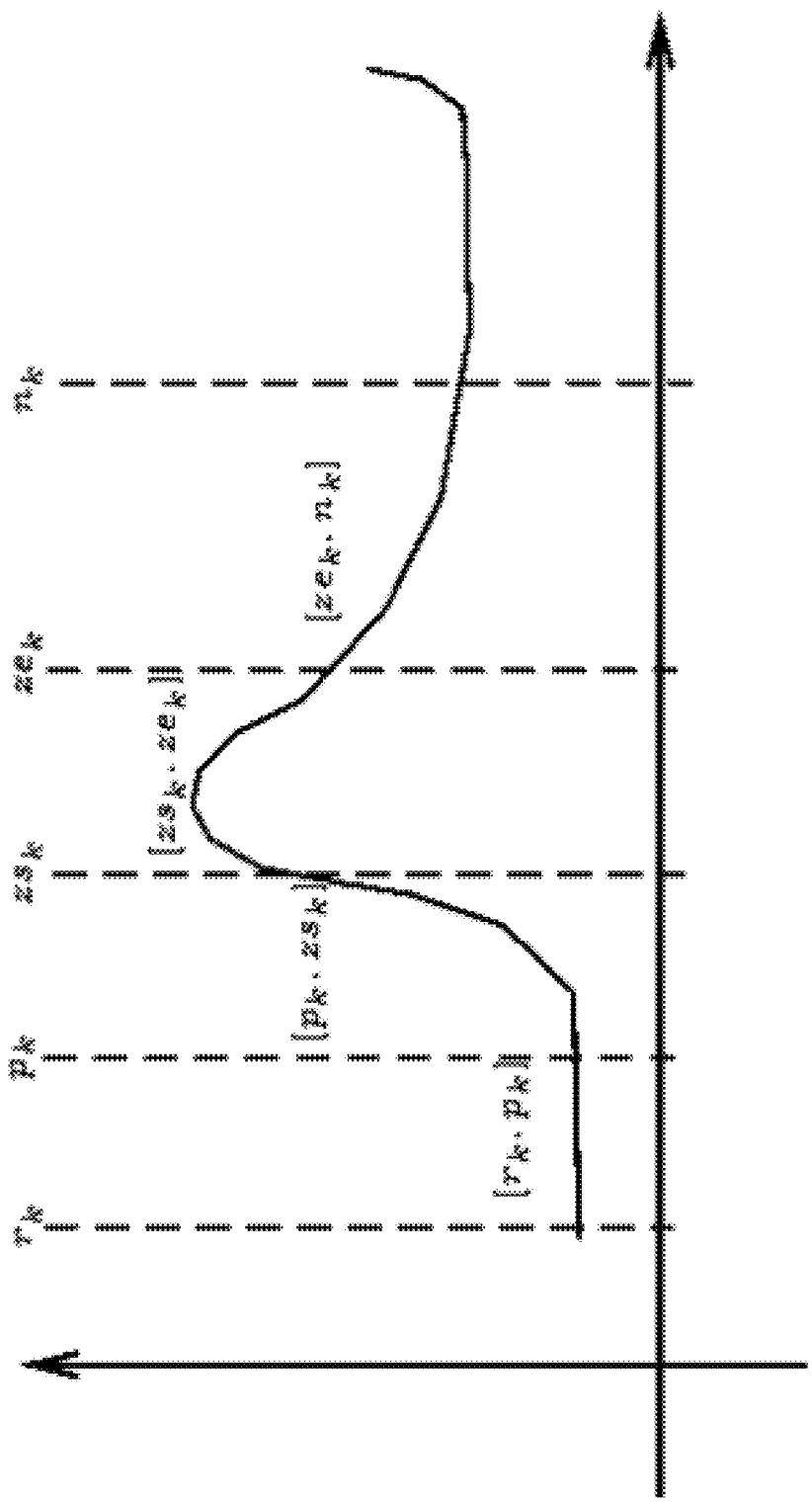
FIG. 6 is a graph illustrating subsections of the signal in FIG. 5 of an event including positive, zero and negative derivatives for illustrating local maxima and minima of a signal in accordance with an embodiment of the invention.
Figure 7:
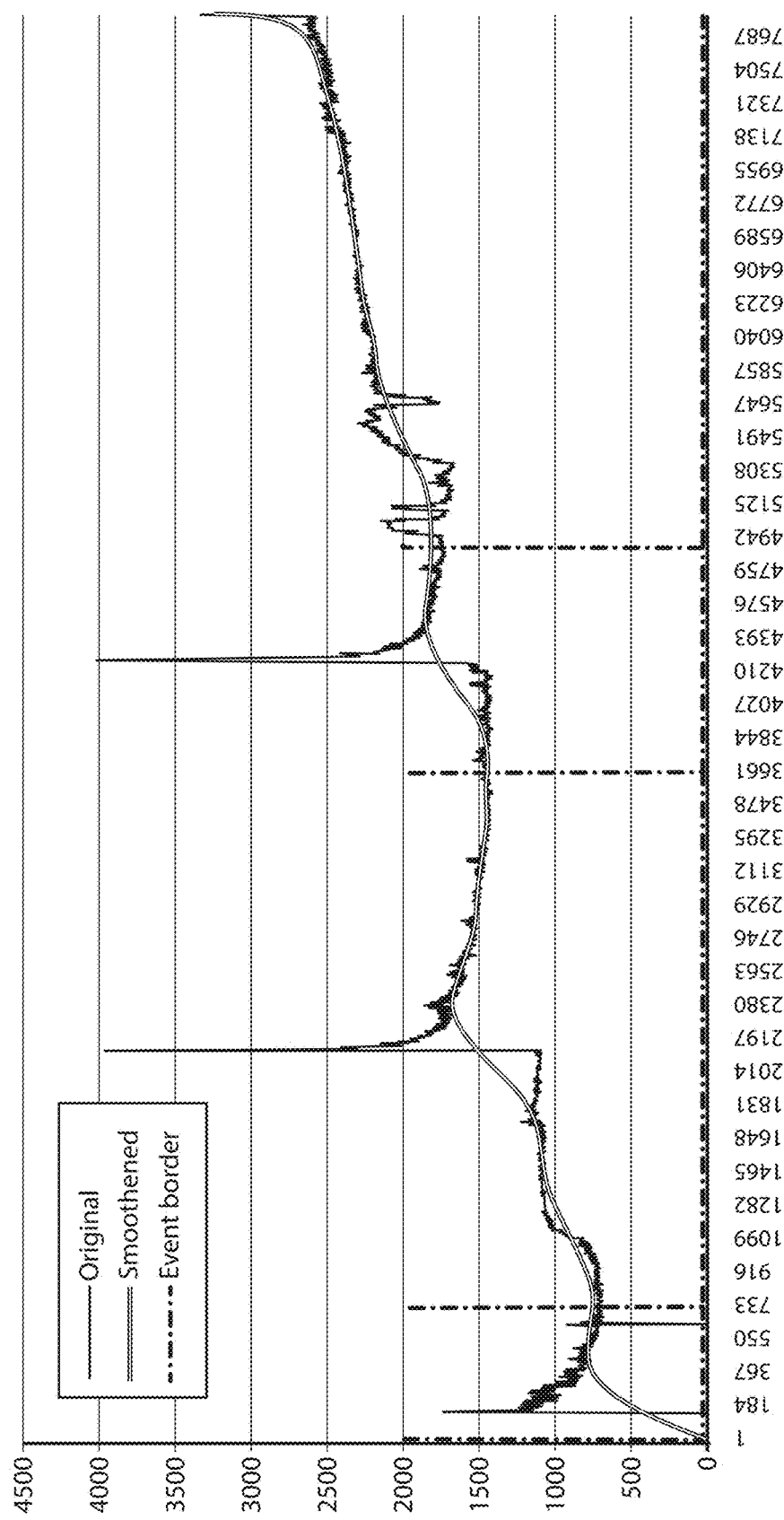
FIG. 7 is a graph illustrating detected events in a sequence of events from sensor data representative of events occurring in an absorbent article in accordance with an embodiment of the invention.

The derivative of each point on the sensors' data gives the trend of the signal. The events are detected by finding the local maxima of the signal. In a differentiable function, critical points represent either local minima or maxima. To rule out the local minima, as they do not represent the events, the trends before and after the critical points are considered. An event starts with a positive derivative which shows an event is starting to happen. Then before the signal comes down, there is a period of time that the derivative is close to zero (theoretically zero). FIG. 6 illustrates the period of closed interval $[p_k, n_k]$ for an event k, sub periods of $[p_k, zs_k]$, $[zs_k, ze_k]$ and $[ze_k, n_k]$ with positive, zero and negative derivatives, respectively. FIG. 7 shows the detected event for a sample raw sensor's data.

Generating the Representative Vector

Figure 8:
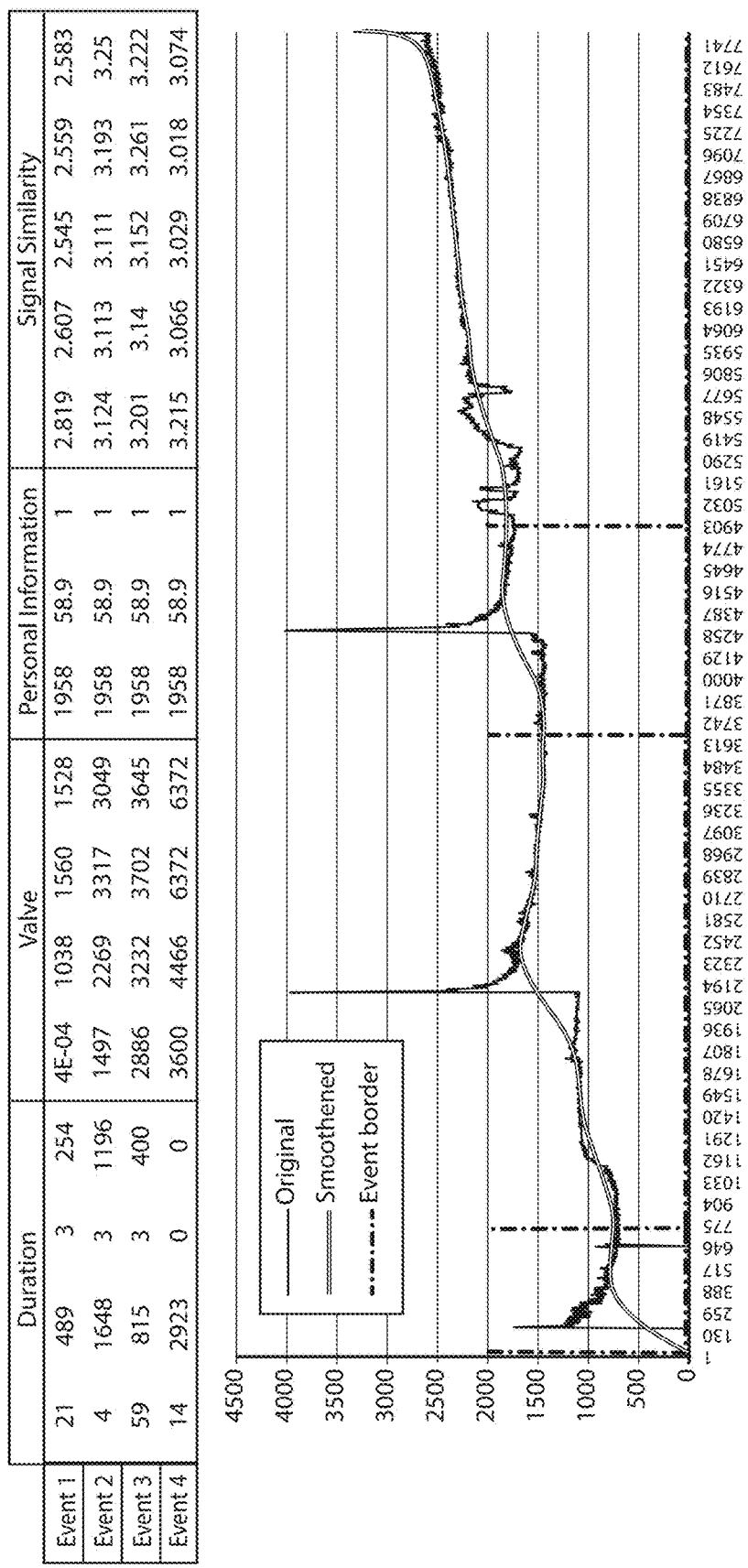
FIG. 8 is a table and a graph illustrating elements of representative vectors for a sequence of events occurring in an absorbent article in accordance with an embodiment of the invention.

Instead of dealing with the events in their signal form, it is much easier to convert each event to its representative vector. This vector, $\overline{rep}$, reflects the properties of the signal. A number of factors introduced as effective factors are as follows: age, weight, gender (both demographic factors), duration and average value of relax part, duration and average of increasing part, duration and average of decreasing part and similarity of each signal to an accumulated signal which is a sum of all of the signals generated by the sensors in the absorbent article. The similarity measure enables the algorithm to detect signal artefacts or noise such as "wetbacks" or faecal matter exudates as opposed to urinal exudates. Other elements that are introduced are elements that are subjective and based e.g. on experts' suggestions. FIG. 8 illustrates the elements of representative vectors relating to four events.

Also, each event affects the behaviour of the absorbent article in each sequence of events occurring in the absorbent article. Thus, the sensors' data for each event is dependent on previous events in a sequence and the event itself. Hence, the motivation for taking the previous events into consideration in addition to the event itself. The recursive structure of each event with its history is as following (1).

$$EwH(E_g) = (E_g, C(EwH(E_g-1)))$$

where (1) g=1, EwH $(E_1) = (E_1)$ and where C (Eg) represents a function which returns the cluster type of event Eg. So for example if we have four events in a sequence, all the first, second and third events have effect on the fourth one.

Normalizing

The representative vector contains different elements with different natures. This vector does not really show the behaviour of the signal for one element in comparison to other signals for other elements or the same element if they have different ranges for each element. Normalization allows data, such as signals, on different scales to be compared, by bringing them to a common scale. So to give the same priority to all the elements, all elements are mapped into a same range, represented by $\overline{norm}$. For a mapping function of n variables in a form of $MsR^n$-$[0,1]^n$, the minimum and maximum values of each factor are mapped to 0 and 1, respectively.

Learning Phase

In the Learning Phase, the following process is carried out:

Searching for the Optimum Weight Vector

The elements of the representative vectors have different importance for the void event analysis. This is due the fact that it is hard to say how effective is a factor for void event analysis. Thus, an optimisation method is employed to detect a numeric value or coefficient that represents the importance of each element. So, even if an element is not effective at all for void event detection and analysis, the optimization method will return zero as the effectiveness (weighting) of that element. So it is not necessary to consider that element to find the effective element and can be effectively excluded such that only effective elements are considered.

The optimisation method searches for an input vector, w, in the search space such that the system's output (reaction) reaches the minimum. In such problems a local minimum is not acceptable and the optimisation method should be able to avoid being trapped in local minima and return a global minimum solution instead. The formulation of the global minimization problem is as follows:

$$y = \min f(w)$$

$$f: R^n \rightarrow R,$$

where f(w) is a non-convex real-valued unknown system. Note that there is no need to investigate a global maximization problem separately, since it can be converted to a global minimization problem:

$$\max f(w) = -\min[-f(w)]$$

$$f: R^n \rightarrow R.$$

In here f( ) calculates the error between the observed and the actual volumes (2).

$$\min\left(\sum_{p=1}^{p\_max} \sum_{g=1}^{g=g\_max_p} f(E_g^p)\right) \quad (2)$$

$$f: R^n \rightarrow R.$$

where p is the absorbent article identifier, p_max is the maximum number of sequences for the absorbent article, g is the event identifier for the absorbent article p and $g\_max_p$ is the maximum number of events in the sequence p.

The objective function Obj to be minimized or maximized is the average error between the observed volumes O and the actual volumes A, given in (3)

$$Obj = \frac{\sqrt{|O_1 - A_1|^2 + |O_2 - A_2|^2 + \cdots + |O_n - A_n|^2 +}}{n} \quad (3)$$

$$e_i = |O_i - A_i|$$

$$\Rightarrow Obj = \frac{\sqrt{\sum_{i=1}^{n} e_i^2}}{n}$$

The optimization problem (2) with the objective function of (3), is tackled by any suitable algorithm.

Clustering

Clustering is the process of grouping each of the individuals of a population into a cluster in such a way that the individuals in each group have similar properties. So the ultimate goal is to group the similar events together, then one can say that the events in each group almost represent the void volumes with almost a same size. The more cluster types are provided, the better approximation that is obtained. The information that obtained after clustering is how similar each of the individual events are in comparison to each other. So it is very likely that two individual events in one cluster have the same volume, but the question of how much urine volume each event produces cannot be answered in this phase.

Figure 9:
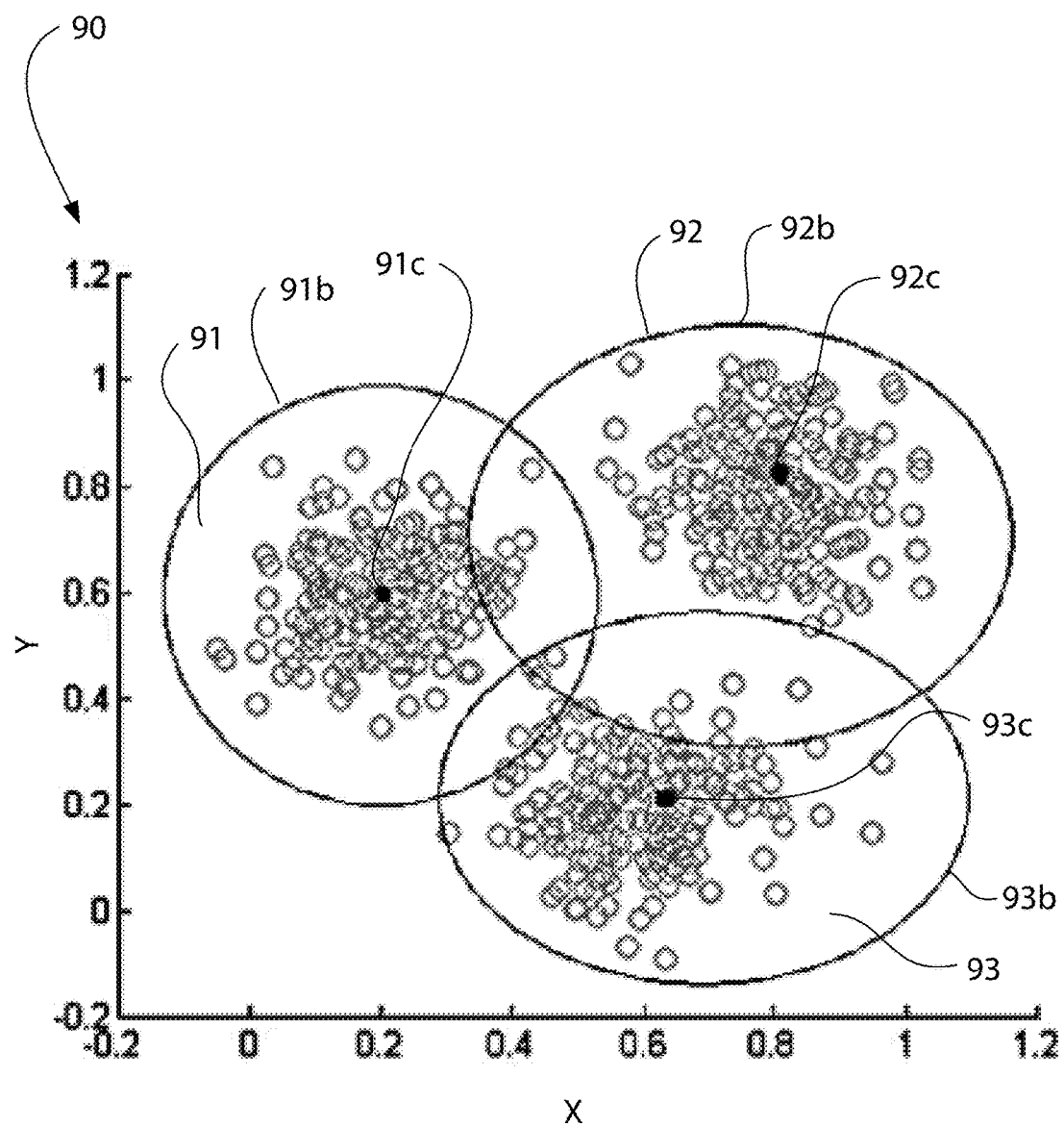
FIG. 9 is illustrates a plurality of weighted representative vectors plotted on a graph as well as group or cluster boundaries and group or cluster centers.

In one form, the algorithm groups similar weighted representative vectors according to a degree of belief of their relative similarity. This form of the invention involves a methodology known as fuzzy clustering. In fuzzy clustering, the individual events do not necessarily belong to just one cluster but to many clusters with a degree of belief. This makes the clustering results more promising as there are some cases where is hard to say if one individual representative vector exactly belongs to a single cluster or group. Instead, an individual event may belong to two or more clusters. FIG. 9 illustrates an example of clustering with 3 clusters 91, 92, 93. FIG. 9 illustrates a plurality of weighted representative vectors plotted on a graph 90 as well as the three clusters 91, 92, 93. Each one of the clusters 91, 92, 93 includes a centre 91a, 92a, 93a or a reference weighted representative vector and a boundary 91b, 92b, 93b. The closer a weighted representative vector of an individual event is to the centre 91a, 92a, 93a of one of the clusters 91, 92, 93 the higher the degree of belief that the event belongs to that cluster relative to the degree of belief that it belongs to another cluster.

During the learning phase, each one of the clusters 91, 92, 93 is allocated a characteristic value, such as a volume amount, which is in turn allocated to each of the weighted representative vectors that are grouped into that cluster.

Fuzzy clustering involves allocating a weighted representative vector obtained during either the learning phase or during the assessment phase to more than one cluster with a degree of belief of belonging of the weighted representative vector to each of the clusters. For example, in a scenario where there are three fuzzy clusters $x_1$, $x_2$ and $x_3$ each having a reference weighted representative vector representing the centre of each fuzzy cluster and where a weighted representative vector of an actual event detected during either the learning phase or the optimisation phase is compared with the fuzzy clusters a degree of belief of belonging of the weighted representative vector to each of the clusters is determined as a function of how close the weighted representative vector is to the centres of the fuzzy clusters. The degree of belief of belonging of the weighted representative vector to each of the clusters is represented by a coefficient between 0 and 1 wherein the total of the coefficients of the degrees of belief for a weighted representative vector equal 1. Thus, for example, the degree of belonging of the weighted representative vector to fuzzy cluster $x_1$ may be 0.2, to fuzzy cluster $x_2$ may be 0.5 and to fuzzy cluster $x_3$ may be 0.3. The sum of the coefficients 0.2, 0.5 and 0.3 must be 1.

Fuzzy c-means (FCM) is way of fuzzy clustering. The aim in FCM is to determine, with soft clusters, that each element has a degree of belongness. To find the optimized clusters, FCM minimizes the degree of belief for the elements which do not really belong to a cluster and increases the belief degree for the elements which actually belong to a cluster. The optimized degree of the belief for the elements can be obtained by the following mathematical optimization problem (4):

$$\min \sum_{j=1}^{c} \sum_{i=1}^{n} m_{i,j} |x_i - c_i|^2 \qquad (4)$$

where $m_{ij}$ is the membership degree of $x_i$ in cluster $c_j$. The algorithm starts from set of random $m_{ij}$ and then minimizes or maximizes the objective function in (4) with an iterative approach. The stopping criterion is usually, either the maximum number of the iterations or the difference between the two consecutive of the objective values.

Fuzzy Neural Network

Training of a fuzzy neural network is adopted to capture the knowledge of fuzzy clustering. As mentioned above, during the learning (optimization) phase when the fuzzy clustering occurs, each weighted representative vector representing an event is categorised in one or more of the fuzzy clusters with a degree of belief of belonging to the one or more fuzzy clusters represented as degree of belief coefficients. The information that is obtained from the fuzzy clustering process carried out during the learning phase, as described above, can be used to train a neural network. Thus, during the assessment phase the trained neural network can approximate the degree of belief of belonging of a given weighted representative vector, which is representative of a detected event, to each of the clusters and thereby approximate a characteristic of the event, such as the void volume of the event. The fuzzy neural network is trained with input information and output information from the fuzzy clustering process. In particular, the fuzzy neural network is trained with input information in the form of the weighted representative vector information for each of the events included in the learning phase and with output information in the form of the degree of belief coefficients for each of these weighted representative vectors representing the degree of belief of belonging of the weighted representative vectors to each of the fuzzy clusters.

For example, if during the learning or optimisation phase there are 200 representative event vectors representing 200 events, namely the input information, then there are 200 sets of degree of belief data representing degree of belief of belonging of the representative vectors to the fuzzy clusters, namely the output information. The fuzzy neural network is trained with this input and output information such that during the assessment phase when a new representative event vector is obtained from sensor data representative of a new event then the degrees of belief information regarding this new representative vector, namely the coefficients representing the degree of belief of belonging of this event to one or more of the fuzzy clusters, can be approximated by the trained fuzzy neural network.

Figure 15:
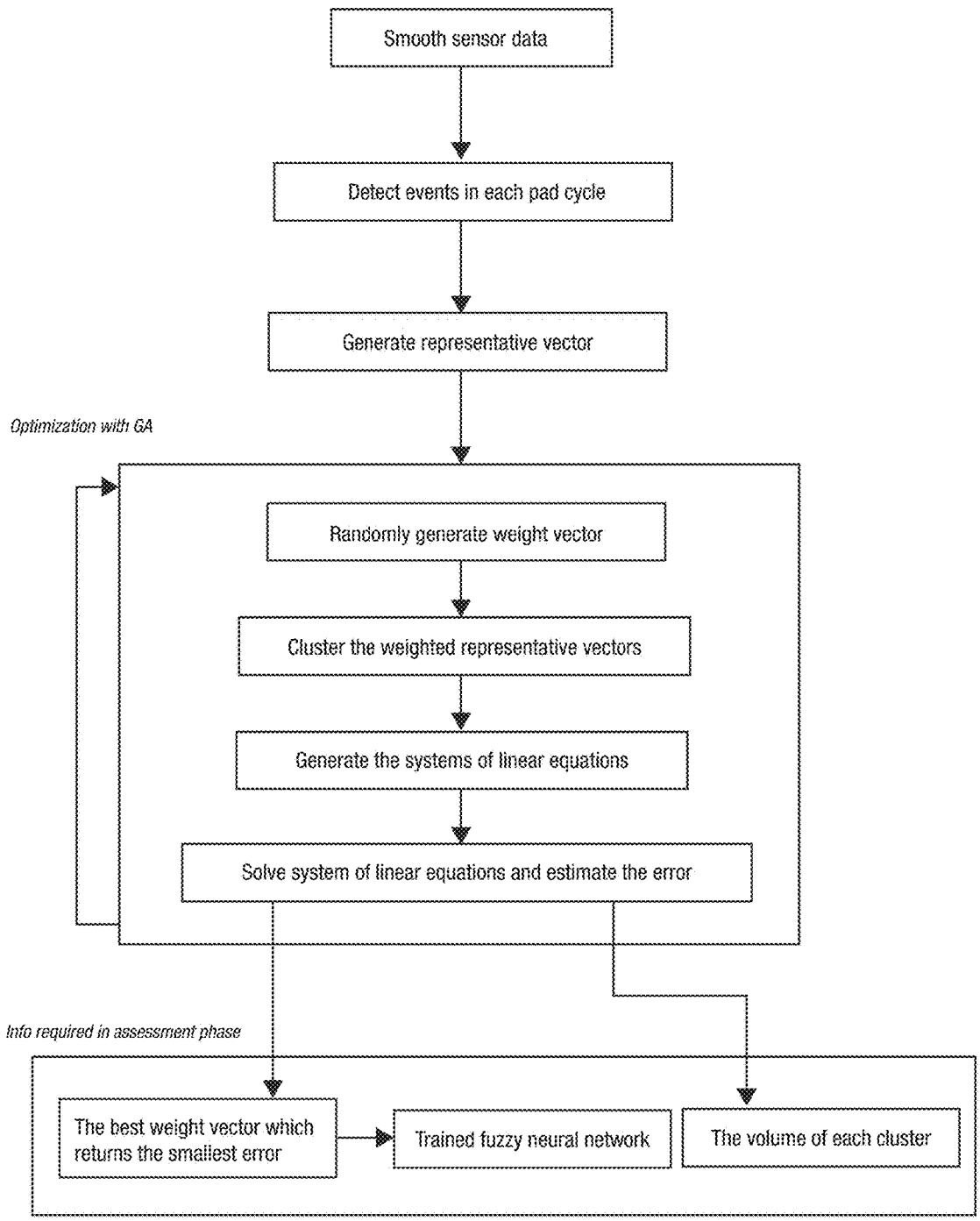
FIG. 15 illustrates a flow chart representing the overall process of the Learning Phase in accordance with an embodiment of the invention.

The flowchart illustrated in FIG. 15 represents the overall process of the Learning Phase as exemplified above.

Accordingly, FIG. 15 illustrates a general flowchart of the voiding event detection and analysis algorithm including training the fuzzy neural network.

Signal Artefacts, Signal Noise and Outliers

The accuracy of the optimized representative parameters obtained during the learning phase can be adversely affected by the input of signal artefacts or noise during the learning phase. Such signal artefacts or noise could be representative of false event signals relating to environmental events such as patient movement, "wetbacks" resulting from patient movement or faecal matter exudates as opposed to urinal exudates. The representative vectors that are representative of "wetbacks" or faecal events may be referred to as wetback representative vectors and faecal representative vectors.

Other signals received during the learning phase that are representative of events occurring in absorbent articles may result in representative vectors that, whilst representative of genuine events, lay far outside the range of the clusters generated during the learning phase. Representative vectors for genuine events may be considered to lay far outside the range of the clusters generated during the learning phase because they have been determined by the method to have a low degree of confidence of belonging to the fuzzy clusters generated during the learning phase and, therefore, may have little or no statistical significance. Such representative vectors may be referred to as outlier representative vectors.

Embodiments of the method can increase the accuracy of the optimized representative parameters obtained during the learning phase to be employed in the assessment phase by, for example, identifying and either quarantining or eliminating wetback representative vectors, faecal event representative vectors and outlier representative vectors from the representative vectors incorporated into the method during the learning phase. Failing to quarantine or remove wetback representative vectors, faecal event representative vectors and outlier representative vectors may bias the parameters of the objective function determined during the learning phase. Accordingly, identifying and quarantining or removing wetback representative vectors, faecal event representative vectors and outlier representative vectors by either discarding or by clustering the wetback representative vectors, faecal event representative vectors and outlier representative vectors in clusters other than genuine event representative vector clusters reduces any bias during the learning phase. It would also be desirable to be able to identify representative vectors relating to wetbacks, faecal events or outliers with a high degree of confidence, during the assessment phase.

By determining the level (or degree) of confidence that a weighted representative vector belongs to the one or more fuzzy clusters of genuine voiding event representative vectors both during the learning phase and the assessment phase it is possible to detect representative vectors that have a low level of confidence of belonging to any one or more of the fuzzy clusters of representative vectors of genuine voiding events. Information about the level of confidence that a weighted representative vector belongs to the one or more fuzzy clusters is a value representing the similarity, or lack thereof, of the weighted representative vector to any one of the fuzzy clusters. In contrast, the degree of belief of belonging information allocated to the representative vector during the fuzzy clustering process of the learning phase is a value representing the relative closeness of a weighted representative vector to all of the fuzzy clusters of which it is eligible to be a member. It is to be appreciated, however, that degree of belief of belonging and level of confidence information can be related such that both sets of information can be derived from a single value or source of information or that one could be derived from the other.

For example, weighted representative vectors representative of wetback events, faecal events or outliers will have allocated to them coefficients of degree of confidence of belonging to genuine event representative vector clusters based on their absolute closeness to each of the clusters. With this information, the method determines which of the weighted representative vectors have less than a predetermined threshold coefficient value for degree of confidence of belonging to any one of the clusters of genuine events. Such weighted representative vectors with less than the threshold coefficient value for degree of confidence of belonging to any one of the clusters of genuine events may be representative of wetback events, faecal events or outliers. On the other hand, where the method includes separate clusters for representative vectors representative of wetback events, faecal events or outliers then the method will determine that weighted representative vectors representative of wetback events, faecal events or outliers respectively belong to these clusters with a high degree of confidence.

Clustering weighted representative vectors that are deemed with a relatively, or sufficiently, high degree of confidence to be representative of wetback events, faecal events or outliers in respective clusters during the learning and assessment phases increases the accuracy of the system in predicting the voiding event volumes of genuine voiding events. Another advantage of clustering weighted representative vectors that are deemed with a relatively, or sufficiently, high degree of confidence to be representative of wetback events and faecal events in respective clusters enables the method to determine wetback events and faecal events occurring in an absorbent article during the assessment phase.

An event which is allocated by the method with a low degree of confidence of belonging to any of the genuine event representative vector clusters could be deemed to be an outlier. It may be an outlier because of confounding factors such as patient movement or other factors. Furthermore, an embodiment of the invention can include clusters associated with outliers such that one outlier cluster might with a high level or degree of confidence relate to faecal matter events and another may relate to wetback events and another outlier cluster for outliers which have a low level or degree of confidence that a weighted representative vector belongs to any of the other clusters.

Generating the System of Linear Equations

A set of linear equations with the same variables make system of linear equations. A solution vector to this system of linear equations is a vector which almost satisfies all the equations.

Each event sequence can be represented by a linear equation which has set of volumes and consequently the overall volume as given in (5).

$$V(E_1^p) + V(E_2^p) + \ldots + V(E_g^p) + \ldots + V(E_{p_{max}-1}^p) + V(E_{p_{max}}^p) = V(p) \quad (5)$$

where p is the event sequence identifier and pmax is the maximum number of the events in the event sequence p.

In general there are $\text{Tote} = \Sigma_{p=1}^{Tot_p} = p_{max}$ events in (5) which can form a system of linear equations as given in as below.

$$\begin{cases} V(E_1^1) + \cdots + V(E_g^1) + \cdots + V(E_{1_{max}}^1) = V(1) \\ V(E_1^2) + \cdots + V(E_g^2) + \cdots + V(E_{2_{max}}^2) = V(2) \\ \vdots \\ V(E_1^p) + \cdots + V(E_g^p) + \cdots + V(E_{p_{max}}^p) = V(p) \\ \vdots \\ V(E_1^{Tot_e-1}) + \cdots + V(E_g^{Tot_e-1}) + \cdots + V(E_{Tot_e-1_{max}}^{Tot_e-1}) = V(Tot_e-1) \\ V(E_1^{Tot_e}) + \cdots + V(E_g^{Tot_e}) + \cdots + V(E_{Tot_{e_{max}}}^{Tot_e}) = V(Tot_e) \end{cases}$$

where the solution to the above system of linear equations gives the estimation of volume for each event.

Considering the clustering done in the previous phase with n clusters for each event category, the above system of linear equation can be translated to a system like:

$$\begin{cases} V(c_{1,1}) + \cdots + V(c_{2,4}) + \cdots + V(c_{n,2}) = V(1) \\ V(c_{1,4}) + \cdots + V(c_{1,2}) + \cdots + V(c_{n,3}) = V(2) \\ \vdots \\ V(c_{1,3}) + \cdots + V(c_{2,4}) + \cdots + V(c_{n,4}) = V(p) \\ \vdots \\ V(c_{1,2}) + \cdots + V(c_{2,3}) + \cdots + V(c_{n,1}) = V(Tot_e-1) \\ V(c_{1,1}) + \cdots + V(c_{2,1}) + \cdots + V(c_{n,4}) = V(Tot_e) \end{cases}$$

where ci,j is the cluster j of the event category i. Solving the above system of linear equations provides the solution vector which represents the volume for each cluster. The best weight vector sought in the learning phase ultimately reduces the error of the solution for the above system of linear equations.

Assessment Phase

In the Assessment Phase, the following process is carried out:

1. Smoothing: The sensors signals are smoothened every w-t minutes. The smoothing technique is ideally the same as the one used in the learning phase.
2. Event detection: The events from the beginning of the sequence are detected.
3. Generating the representative vector: The representative vector for each event is made. The elements which are considered in the first phase should be applied in generating the representative vector during the assessment.
4. Normalizing: The elements of the representative vectors are normalized.
5. Prioritizing factors: The optimum weight vector w sought in the learning phase is multiplied to each of the elements in the representative vector, known as the weighted representative vector. The resulting weighted representative vector emphasizes the important elements for the cluster detection phase.
6. Cluster detection: The best cluster for each of the weighted representative vectors is then detected. To be able to find the cluster, the centres of the clusters which are the same as the ones obtained in the learning phase are applied. In an alternative embodiment, during the assessment phase, the weighted representative vectors representative of sensor detection of new events are allocated degree of belief coefficients by the trained neural network.
7. Generating the linear equation: Now each event type has a cluster in its event category. So a linear equation of form (6) for the event sequence can be converted to a form of (7):

$$V(E_{w-t}^P) + V(E_{2,w-t}^P) + \ldots + V(E_{now}^P) \quad (6)$$

$$V(c_{1,i}) + V(c_{2,j}) + \ldots + V(c_{n,k}) \quad (7)$$

The value for Equation (7) can be calculated by having the solution from the learning phase.

Embodiments of the system of the invention involving the use of a neural network enables the system to approximate more accurately the value, or volume of exudate, associated with the event that the weighted representative vector represents as a weighted average of the cluster volumes determined with reference to the respective coefficients of degree of belief belonging of the weighted representative vector to each of the clusters. This means a void volume amount of a detected event need not be approximated to only one cluster value, but may be approximated by a weighted combination of cluster values, giving rise to more accurate estimates.

Verification or Testing of the Optimised Objective Function

In embodiments of the invention, a further process is involved in which the accuracy or appropriateness of the optimal mathematical model obtained during the optimisation phase is verified. In other words, the correctness of the optimal mathematical model obtained from the optimisation process is proved or disproved. Verification or testing of the optimal mathematical model can be included as an additional step or phase during the learning or optimisation phase to verify the correctness of the optimal mathematical model determined during the learning phase. In an embodiment, the step of verification includes dividing the data set used for the learning phase into a learning data set and a testing data set such that the learning and testing data come from the same set of data. For example, the learning data set and the testing data set are taken from the same overall set of absorbent pad cycles and observation data used obtained during the learning phase.

The testing phase involves adopting the optimised mathematical model to estimate voiding event volumes for the voiding events in the testing data set and thereby determining estimates of the cumulative volumes of the event cycles in the absorbent pads of the testing data set. The estimates of the cumulative volumes of the event cycles of the testing data set are compared with the observation data namely the actual, measured cumulative volumes of voiding events in each sequence in each absorbent pad. The extent to which the optimal mathematical model accurately estimates voiding event volumes in the sequences of events of the testing data set reflects the correctness of the optimal mathematical model determined during the learning phase. If the optimised mathematical model provides estimates that are inaccurate because they involve an error that is more than a predetermined acceptable error then the learning phase may need to be carried out again with a new learning data set or the mathematical model may require modification. If the optimised mathematical model provides estimates that are accurate because they involve an error that is less than a predetermined acceptable error then the mathematical model obtained during the learning phase may be adopted in the assessment phase.

Hierarchical Optimisation

In embodiments of the method the process of determining an optimal mathematical model during the learning phase can be deliberately influenced by utilising a hierarchical optimisation method. In one form of this method, a hierarchy of factors that are deemed to have greater or lesser significance to the estimates to be made by the optimised objective function are determined depending on the intended use and outcomes of the system. In another form of this method, a hierarchy of objective functions of the mathematical model to be optimised is determined. The hierarchy of objective functions can be determined as those objective functions of the mathematical model deemed to have greater or lesser importance to the intended use and outcomes of the method. Thus, the hierarchical optimisation method involves influencing the weightings given to elements of the representative vectors or to representative vectors themselves in order to influence the learning phase to produce an optimised mathematical model in which certain objective functions which are deemed to have more importance are optimised in preference to other objective functions deemed to have lesser importance.

For example, if the optimised mathematical model obtained during the learning phase is intended to produce estimates of voiding event volumes based on sensor data from absorbent pads received during an assessment phase in the context of an aged care facility there may be a number of outcomes of the method that are deemed more important for the method to be accurate in estimating than others. For example, in an aged care facility, one of the most important factors for accurate estimating is the correct time to change the absorbent pad of a patient. The correct time to change an absorbent pad may depend on the size and construction of the pad in question. Assuming the absorbent pads used during the assessment phase should be changed when the cumulative volume of voiding events in the pad is between 100 mL and 200 mL then the correct time to change assessment made by the optimised mathematical model is when the estimated cumulative volume of events in an absorbent pad is between 100 mL and 200 mL or whatever range is appropriate for the type of absorbent pad in question.

A less important factor than correct time to change may be underestimation by the method of the actual cumulative volume of voiding events that have occurred in an absorbent pad. In particular, estimation of the cumulative volume being within the correct time to change range, for example between 100 mL to 200 mL, where in actual fact the actual cumulative volume in the absorbent pad is greater than the limits of the range, for example greater than 200 mL. Underestimation is undesirable because it may result in a patient being forced to wear an absorbent pad than has absorbed more urine than its designed limit.

A less important factor than both correct time to change and underestimation may be overestimation by the method of the actual cumulative volume of voiding events that have occurred in an absorbent pad. In particular, estimation of the cumulative volume being within the correct time to change range, for example between 100 mL to 200 mL, where in actual fact the actual cumulative volume in the absorbent pad is less than the limits of the range, for example less than 100 mL. Overestimation is undesirable because it may result in a patient having their absorbent pad changed when changing is not required. However, overestimation may more tolerable than underestimation because it may be considered more tolerable for a patient to have their absorbent pad changed when changing is not required than it is for a patient to be allowed to be in the situation of wearing an absorbent pad that has received more than its maximum limit of urine and well after the point at which the absorbent pad should have been changed. Thus, in the present example, overestimation may be lowest in terms of objective functions of the mathematical model to be optimised. Underestimation will be given higher priority in the hierarchy of objective functions to be optimised than overestimation but not higher than correct time to change which will be given the highest priority of the objective functions to be optimised.

Thus, during the learning phase, the above hierarchy of objective functions to be optimised is included in the process by which the mathematical model is optimised such that the accuracy of the model, optimised during the assessment phase, is optimised firstly for estimating the correct time to change, secondly for avoiding underestimation and lastly for avoiding overestimation. By employing a hierarchy of objective functions to be optimised in the course of optimising the mathematical model during the learning phase the weightings allocated to elements of the representative vectors, and perhaps other factors, are biased in favour of achieving the best outcome in terms of the hierarchy of outcomes determined for the method.

Testing Protocol

The present invention provides a method and a system for monitoring wetness in one or more absorbent articles such as pads, diapers, adult incontinence garments or the like. In embodiments of the method and the system, a learning phase is carried out in which information is derived from sensors incorporated in absorbent article such as pads, diapers, adult incontinence garments or the like for detecting wetness resulting from urinary and faecal incontinence events. In the learning phase, the method involves: receiving sensor signals representing a plurality of events in each of one or more absorbent articles; receiving observation data describing a characteristic of the plurality of events in an absorbent article; identifying an optimal mathematical model describing a relationship between the sensor signals and the observation data.

The accuracy of the optimized mathematical model obtained during the learning phase in allocating a characteristic to an event represented by the sensor signals, such as the volume of a voiding event, can be affected by variables such as absorbent pad specification, design, composition and structure or wetness sensor specification, design, composition and structure. Other variables that may affect the accuracy of the optimized mathematical model obtained during the learning phase in allocating a characteristic to an event represented by the sensor signals may be the means with which the sensors are fixed or manufactured into the absorbent pad, the number and location of the sensors relative to the absorbent pad and other structural parameters of the absorbent pad and sensor combination. Yet more variables that may affect the accuracy of the optimized mathematical model obtained during the learning phase in allocating a characteristic to an event represented by the sensor signals may be the means with which the sensor signals are received from the sensors such as through hard-wires or a wireless system. Another variable that may affect the accuracy of the optimized mathematical model obtained during the learning phase in allocating a characteristic to an event represented by the sensor signals may be the actual mathematical model itself.

For example, variables such as different adhesive methods and adhesives used to retain wetness sensors to an absorbent pad and different absorbent pad structures, sizes, and compositions, sensor types and modes of manufacture may impact on the effectiveness of signals received from the sensors in developing an optimised mathematical model obtained during the learning phase that is capable of accurately estimating a volume of a voiding event occurring in the absorbent article during an assessment phase. In another example, those variables may impact on the effectiveness of signals received from the sensors in enabling the optimised mathematical model obtained during the learning phase to accurately estimate a volume of a voiding event occurring in the absorbent article during an assessment phase.

An embodiment of the method, described herein, is able to determine the impact that different variables, including but not limited to the above variables, may have on the accuracy of the optimized mathematical model, obtained during the learning phase, in allocating a characteristic to an event represented by the sensor signals, such as the volume of a voiding event during the learning and assessment phases. An embodiment of the method is also able to determine whether changes or improvements to the above variables or how they are represented in the mathematical model have the effect of improving the accuracy of the optimized mathematical model, obtained during the learning phase, in allocating a characteristic to an event represented by the sensor signals during the learning and assessment phases.

In an example, a laboratory testing protocol is established whereby, for example, for a single absorbent pad type there are two or more sets of absorbent pads each set of absorbent pads includes a different adhesive method for attaching a set of wetness sensors to the absorbent pads. For example, one of the sets of absorbent pads includes 24 locations at which adhesive is used to attach wetness sensors to each absorbent pad and another one of the sets of absorbent pads includes 88 locations at which adhesive is used to attach wetness sensors to each absorbent pad. In both sets of absorbent pads identical wetness sensors are included. The purpose of the testing protocol is to establish whether one of the sets of absorbent pads when used in the learning phase of the method described above results in a mathematical model that more accurately estimates the volume of a wetness event occurring in the absorbent pad during the verification step of an embodiment of the method or during the assessment phase of another embodiment of the method. A similar testing method may be employed to verify the accuracy of the mathematical models employed for pad/sensor combinations arising from a range of manufacturing methodologies.

In the example, a laboratory testing rig is used in which for each of the first and second sets of absorbent pads, which in the example includes a set of identically constructed absorbent pads for each set, each absorbent pad is mounted in a stable and repeatable manner and a wetness applicator, such as a syringe, is used to accurately and repeatably apply a variety of predetermined amounts of liquid, such as water or a urine surrogate, to each absorbent pad at a variety of times. Thus, for each absorbent pad a series of wetness events is simulated to provide a simulated cycle of wetness events occurring in the absorbent pad. Sensor signal generated by wetness sensors in each absorbent pad are received and the process is repeated for each of the set of different absorbent pads of each of the first and second set.

The testing protocol of the method may involve using any number of identically constructed absorbent pad and sensor combination sets as long as for each set of absorbent pads and sensor combinations all of the elements of the testing protocol are identical for each set. For example, the amount of simulated voiding events for each absorbent pad and sensor combination is the same for each set, the volume of each simulated voiding event is the same for each absorbent pad and sensor combination for each set, the time between simulated voiding events for each absorbent pad and sensor combination is the same for each set and the testing rig or apparatus is the same for each absorbent pad and sensor combination for each set. Thus, the testing protocol is designed to ensure that, to the extent possible, the only variable that differs between the sets of absorbent article and sensor combinations being tested is the design or manufacturing parameter that is being tested. Furthermore, the testing protocol is ideally designed so that the quantity, distribution and characteristics of the simulated voiding events in the absorbent articles of each set are representative of genuine voiding events that are likely to occur in a clinical or aged care facility environment.

The testing protocol includes, for each set of absorbent pad and sensor combinations, subjecting each absorbent pad and sensor combination to a cycle of simulated wetness events, carrying out the learning and assessment phases of the method of the invention described herein. This includes receiving sensor signals representing the simulated events occurring in the absorbent articles and processing the sensor signals to determine a characteristic of at least one event in the absorbent article. In a preferred form, the step of processing the sensor signals includes identifying in each of the sensor signals one or more different events and, for each different event: (i) generating a representative vector for that event; (ii) allocating weightings to the representative vector to generate a weighted representative vector; and (iii) allocating a characteristic to each weighted representative vector. The method further includes carrying out the learning phase described herein including the step of receiving sensor signals representing a plurality of events in each of one or more absorbent articles and receiving observation data describing a characteristic of the plurality of events in each absorbent article. The learning phase of the method then involves using the sensor signal information and the observation data to determine one or more mathematical models each describing a relationship between the sensor signals and the observation data and identifying an optimal one of the mathematical models and thereby determining optimal parameters of an objective function. In a preferred form, each one of the mathematical models is a system of linear equations describing the relationship between the sensor signals and the observation data.

The above testing protocol is carried out in respect of a proportion of each of the two sets of 117 data sets for each of the 117 absorbent pad cycles, referred to as a learning data set, in order to determine an optimised mathematical model for each absorbent pad and sensor combination. The optimised mathematical model for each absorbent pad and sensor combination is based on a predetermined objective function to be optimised, such as least error for each wetness event estimate, or correct time to change or based on a hierarchy of objective functions to be optimised.

The testing protocol of the method includes a step of verifying the correctness of the optimal mathematical model obtained for each of the absorbent pad and sensor combinations by the above method. This verification step includes adopting the optimised mathematical model obtained for each absorbent pad and sensor combination to estimate voiding event volumes for the simulated voiding events occurring in the remaining proportion, or testing data set, of each of the two sets of 117 data sets for each of the 117 absorbent pad cycles.

The testing protocol of the method thereby determines estimates of the volumes of individual events or cumulative volumes of the event cycles in the absorbent pads of the testing data set. The estimates of the cumulative volumes of the event cycles of the testing data set are compared with the observation data namely the actual, measured cumulative volumes of voiding events in each sequence in each absorbent pad. The extent to which the optimal mathematical models accurately estimate simulated voiding event volumes in the sequences of simulated events of the testing data set reflects the correctness of the optimal mathematical model determined during the learning phase.

Also, a comparison of the extent to which the optimal mathematical models of the two absorbent pad and sensor combinations accurately estimate simulated voiding event volumes in the sequences of simulated events of the testing data set reflects the relative absorbent capacities of the absorbent pad and sensor combinations when used with the method to enables accurate estimates of void event volumes. The overall accuracy with which the method estimates the event volume of each simulated voiding event for each of the two sets of absorbent pads can be statistically compared to determine which of the two absorbent pads enables the method to more accurately estimate the event volume of simulated events. This information can be used to improve the design or method for attaching a set of wetness sensors to the absorbent pads such that the absorbent pad can enable the method to more accurately estimate the volume of a wetness event in a clinical environment or an aged care facility or the like.

As can be appreciated, other embodiments of the method are envisaged in which two or more sets of absorbent pads are compared wherein the sets of absorbent pads and sensor combinations differ from each other with respect to one variable. Such variables could include absorbent pad specification, design, composition and structure or wetness sensor specification, design, composition and structure. Other variables could include the means with which the sensors are fixed or manufactured into the absorbent pad, the location of the sensors relative to the absorbent pad and other structural parameters of the absorbent pad and sensor combination. Yet more variables could include the means with which the sensor signals are received from the sensors, in other words the means by which the sensor signals are delivered from the sensors to a sensor signal input of a system, such as through hard-wires or via a wireless system.

For example, variables could include different absorbent pad sizes designed to contain different volumes of wetness, different adhesive methods and adhesives used to retain wetness sensors to an absorbent pad.

In the above example, the method includes determining the accuracy of the estimates of simulated void event volumes from sensor data from the testing data sets. In the example, objective functions to be optimised by the method is a set of correct time to change volume ranges that are determined as volume ranges within which an absorbent pad should be changed when the method estimates the cumulative volume of a sequence of simulated events occurring in the absorbent pad is within a respective one of the ranges. In the present example, the correct time to change ranges may be e.g.: 0 ml-200 ml, 100 ml-300 ml, 200 ml-400 ml, 300 ml-500 ml, 400 ml-600 ml, 500 ml-700 ml and 600 ml-800 ml. Accordingly, this example of the testing protocol method involves determining the proportion of times that the method correctly estimates that absorbent pads of the two sets of absorbent pads have received a cumulative volume of a sequence of simulated voiding events within one of the correct time to change volume ranges, represented as a percentage, and plots these percentages on a graph, as exemplified in FIG. 10.

Figure 10:
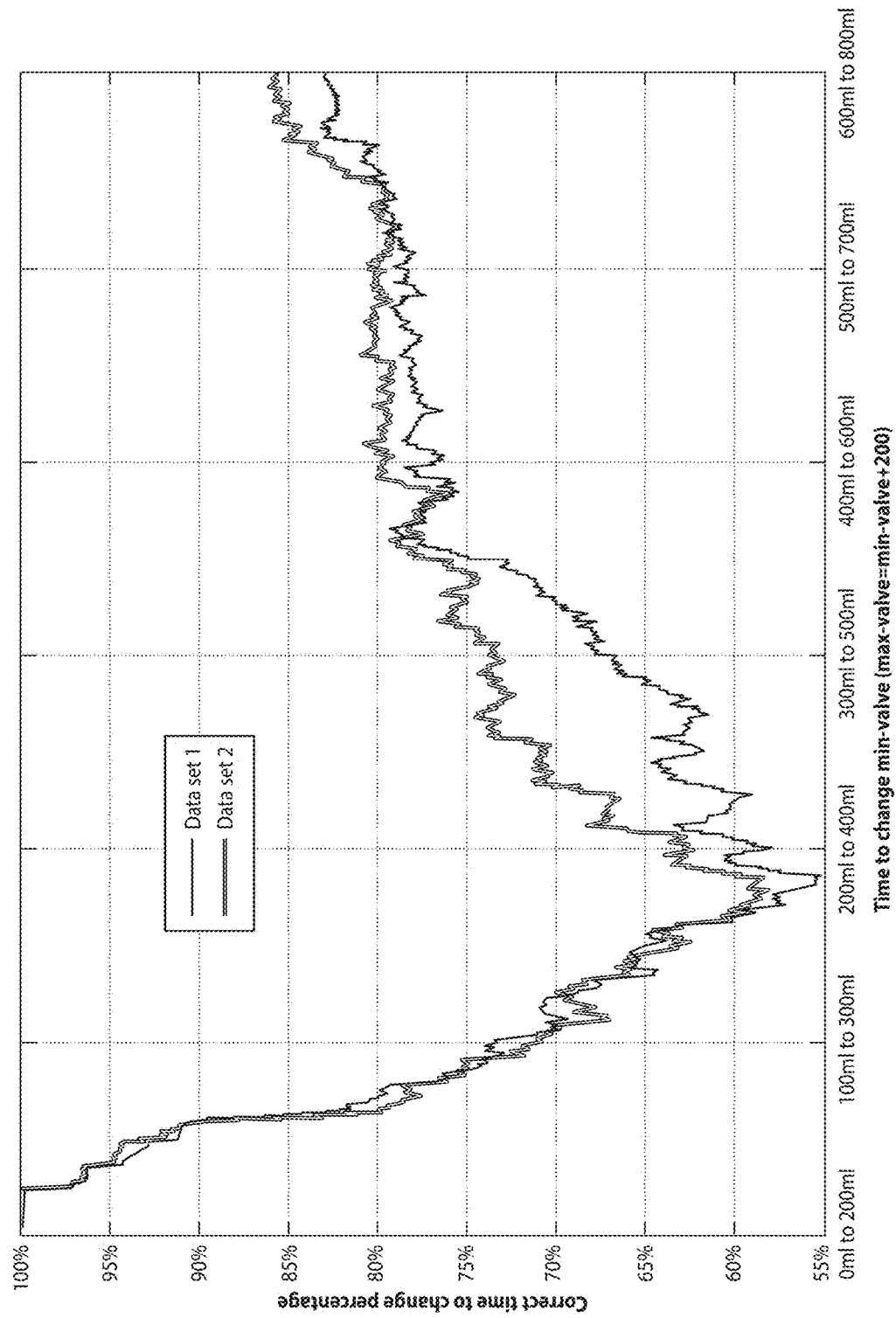
FIG. 10 is a graph plotting the effectiveness of two types of absorbent pad and sensor combinations in enabling the method to accurately determine correct estimates of the correct time to change an absorbent pad.

The two plots in the graph of FIG. 10 represent the relative abilities of the two sets of absorbent pads, of 117 pads each respectively involving 24 and 88 sites on the pad at which adhesive is used to attach wetness sensors to each absorbent pad, to provide sensor signals that enable the method to provide accurate estimates of the cumulative volume of a sequence of simulated voiding events occurring within an absorbent pad falling within one of the correct time to change volume ranges. The information represented in the graph enables a comparison to be made between the two different adhesive options for otherwise identical absorbent pad and sensor combinations for determining which combination is more likely to provide superior results in a clinical environment such as an aged care facility. The above method can be used to determine the relative effectiveness of different absorbent pads, sensors and absorbent pad and sensor combinations for enabling the method to provide accurate void event volume estimates.

Another example of the testing protocol involves testing and comparing the effectiveness of different optimisation methods against each other. In this example, the testing protocol of the method includes, for each mathematical model, employing identical sets of absorbent pad and sensor combinations, subjecting each absorbent pad and sensor combination to a cycle of simulated wetness events and carrying out the learning phase of the method of the invention described herein on the learning data set of the absorbent pad cycles to identify respective optimal optimisation methods. The method includes a step of verifying the correctness of the optimal optimisation method including adopting the optimal mathematical models arrived at by the optimisation method to estimate voiding event volumes for the simulated voiding events occurring in the remaining proportion, or testing data set, of the set of absorbent pad cycles. The overall accuracy with which the respective mathematical models arrived at by the different optimisation methods estimate the event volume of each simulated voiding event for the testing data set can be statistically compared to determine which of the two optimisation methods arrives a mathematical model which more accurately estimates the event volume of simulated events. This information can be used to improve the optimisation method such that the method may more accurately estimate the volume of a wetness event in a clinical environment or an aged care facility or the like.

EXAMPLE

An example demonstrating how it is envisaged that an embodiment of the invention can be practiced will now be described. This Example describes a portable wireless incontinence monitoring system for aged care facilities. Goals of the system include increasing quality of life for the elderly and reducing the work load of caregivers. In contrast to existing incontinence monitoring systems, the present system does not only detect urinary events but it also estimates the voided volume for each event. For optimizing the parameters of a volume estimation model, genetic algorithms are applied and an objective function is introduced for verification of the obtained volume estimation model.

In this example, the hardware components of the system comprise a portable wireless transceiver and a strip with an array of sensors placed in a diaper to measure conductivity of urine. The software components includes a database to record raw data and a volume estimation module which reads the raw data from the database and estimates the volume. To derive the volume estimation model, genetic algorithms are applied to optimize the parameters of the model during a learning phase over the training set in an offline mode. The obtained model is then tested for estimation of the volume for emulation data in a laboratory by simulating field data. For generating the emulation scenarios, the distributions of the variables such as; volume sizes, timing between each event and the number of urinary events per day for the field is taken into account. Moreover a separate objective function has been designed and included in the embodiment of the system, called time to change objective function, to verify the performance of the volume estimation model on the testing data set. The time to change objective function is included to provide a measure which reflects the validation of the system in the market.

System Design and Development

In this example, the incontinence monitoring system comprises a sensor placed into a diaper, and connected to a wireless component. The wireless component is attached to the top of the residents' underwear. The wireless component transmits the sensors' data to a server which collects all the data from all in an aged care facility. The recorded data is then analysed by software and the results are shown to the end user via a user interface. The caregivers can check the residents' status from any workstation in communication with the server to see if the resident has to be changed or not. Also, an alert can be sent to a caregiver's mobile telephone, tablet computer or other mobile communication device. The schematic of the system is illustrated in FIG. 2. The main criteria during the development of the proposed system are defined as follows:

Comfortability for the Residents

A primary concern in designing the system is to provide comfort for the residents. The only extra components in addition to the diaper that each resident wears when monitored using the system are the sensor which is placed into the diaper and a wireless component which is clipped to the top front of the residents' underwear. The sensor, is barely felt by the residents and the wireless component is a small device which weighs less than 30 grams.

Ease of Use for the Caregivers

The system provides a process for caregivers to take care of residents. Typically, the only additional effort required of caregivers is to create a profile for each resident with the user interface via any workstation. This enables the system to keep track of each resident and alert the caregivers when a resident's diaper has to be changed.

Cost and Specifications

The system includes a diaper with a disposable sensor, placed into the diaper. The sensor is connected to a chargeable wireless component, which sends the sensor's data to the server. In the current example, the minimum requirements of the server are 2.40 GHz Intel Core™ 2 Duo processor, 3 GB RAM, 160 GB of hard drive disk, NVIDIA GeForce 8500 GT, or ATI Radeon HD 4350 graphic card with Windows XP Professional SP3. Compatibility of the system is also adapted to be verified on Windows XP Professional SP2, Windows Server 2008 Enterprise 32-Bit, Windows Server 2008 Enterprise 64-Bit. The minimum requirement of the workstations are (Intel® Pentium® III 450 MHz or faster processor (or equivalent)), 2 GB of RAM, with Windows 7, Windows Vista, or Windows XP Service Pack 2.

Volume Estimation as an Optimization Problem

In this section, there is provided a discussion of how to derive the volume estimation model. Then the volume estimation model is used to alert the caregivers when the estimated voided volume reaches a pre-defined capacity of the diaper. The diaper capacity is either defined by the diaper manufacturer or it can be advised by the aged care facilities.

Modelling of the Volume Estimation

An aged care facility resident may void one or more times while he or she is wearing a diaper. The manual process of dealing with incontinence is to check the resident every few hours, and if required, to change the resident's diaper. In the occasion of changing, the caregivers also record the weight of the diaper. The period of time from wearing the diaper to changing it is called a pad cycle. The pad cycle is, therefore, the period of time that data is collected for each diaper. In the present exemplary system, for each pad cycle, raw sensor data along with the resident's weight, demographic information, food and fluid intake information, time of the day, temperature and humidity of the environment and other factors are recorded.

Figure 11:
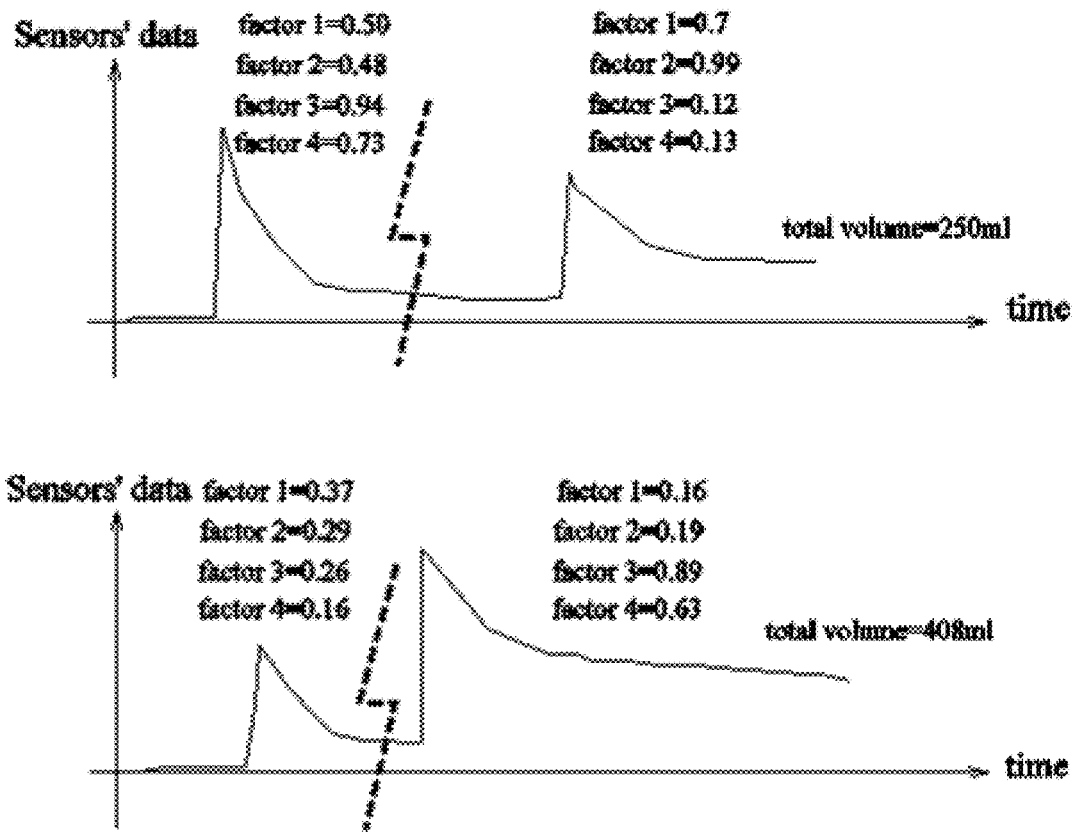
FIG. 11 is a graph plotting two examples of pad cycles with their cumulative volume and their representative factors.

To train a model, each pad cycle is represented with some factors. By introducing different factors the necessary information of the pad cycles is captured. FIG. 11 shows two examples of pad cycles with their cumulative volume and their representative factors. Genetic algorithms are used to tune the parameters of a black box which represents the volume estimation model. This model estimates a volume for each of the representative factors of each pad cycle. The goal is to optimize the parameters of the black box such that the objective function given in (1) is minimized.

$$ave-\text{error} = \frac{\sum_{i=0}^{number\ of\ pad\ cycles} (estimated_i - actual_i)^2}{number\ of\ pad\ cycles}$$

Figure 12:
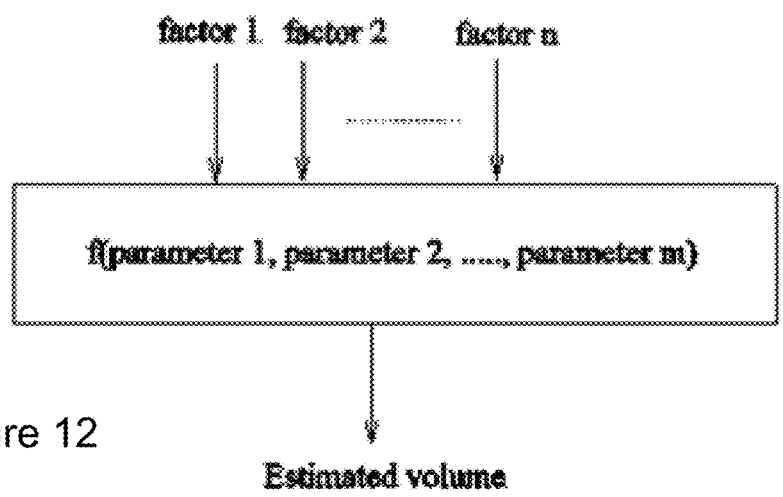
FIG. 12 shows a general structure of a volume estimation model after training with inputs which are the representative factors of each pad cycle and outputs which are expected to be a volume very close to the actual volume in the diaper.

The volume estimation model can be seen as a black box where the inputs are the representative factors of each pad cycle and the output is expected to be a volume very close to the actual volume in the diaper. A model which has the smallest value of the objective function over all the training set is chosen as the volume estimation model. FIG. 12 shows a general structure of a volume estimation model after training.

Time to Change Objective Function

Estimation of the exact volume of urine in a diaper is not very important in aged care facilities. The caregivers' preference is to change the residents when the volume of the urine in the diaper reaches the capacity of the diaper. As an example, the volume estimation model may predict the cumulative volume to be 350 ml when the actual volume is 300 ml. Let us assume the acceptable range of changing the diaper is defined to be 250 ml to 400 ml then for a volume estimate of 350 ml, the system will alert the caregiver to change the diaper. In this case, the caregiver will be satisfied with the performance of volume estimation model, despite the estimated volume having over-estimated by 16%. The acceptable range of changing a diaper is represented by the closed interval of [min_capacity, max_capacity]. On the other hand, if the caregiver receives an alert to change the diaper while the cumulative volume is less than min_capacity or more than max_capacity then they would not be satisfied with the performance of the volume estimation model.

Accordingly, in a preferred embodiment, as exemplified herein a time to change objective function for the verification of the obtained volume estimation model is introduced. The time to change objective function is aligned with what the market, or end user, requires and so is related to validation of the system. So we expect the performance percentage of system validation would be close (or linearly related) to the performance percentage of system verification. The time to change objective function is defined as follows:

Algorithm 1 The time to change objective function if
Both estimated and actual volumes are between [$C_{min}$, $C_{max}$].
OR,
The estimated volume is greater than $C_{min}$ and the actual volume is greater than $C_{max}$, but the actual volume prior to the previous event was less than $C_{min}$.
OR,
Both estimated and the actual volumes are less than $C_{min}$. This is called correct estimation-not full.
then
   The changing alert is correct; (The conditions described within the if statement correspond to scenarios where the caregivers
   would be satisfied with the performance of the volume estimate.)
else if
The estimated volume is less than $C_{min}$, but the actual volume is in [$C_{min}$, $C_{max}$]. This is called under estimation-low risk.
OR,
The estimated volume is less than [$C_{min}$, $C_{max}$], but the actual volume more than $C_{max}$ and the actual volume prior to the previous event was not less than $C_{min}$. This is called under estimation-medium risk.
OR,
The estimated volume is less than $C_{min}$, but the actual volume is more than $C_{max}$. This is called under estimation-high risk.
OR,
The estimated volume is greater than $C_{min}$, but the actual volume is less than $C_{min}$. This is called over estimation.
then
   The changing alert is incorrect; (The conditions described within the else if statements correspond to scenarios where the caregivers would not be satisfied with the performance of the volume estimate.)
end if A very simple implementation of the time to change objective function is to give +1 point for each correct estimation and −1 point for each incorrect estimation. A volume estimation model with higher points is more preferred in the field. Note that the caregivers do not receive any changing alerts for under estimation-low risk, under estimation-high risk, and correct estimation-not full cases. However, the residents get changed after some pre-defined period of time which is called max_period, even though no changing alert message is being sent.

Simulation and Results

The set up of an exemplary emulation in the laboratory and how to generate emulation scenarios is discussed below. Also discussed below is reporting of the system verification results. The emulation environment involves a female dummy wearing a diaper including the sensor connected to the wireless component. Using this set up 119 pad cycles were generated, of which the following is an example:

| Diaper # | Diaper Size | Event Type | Est. Time of Void from start (min) | Void Size (mL) |
|---|---|---|---|---|
| 1 | Heavy | Void | 0 | 61 |
| 1 | Heavy | Void | 20 | 375 |
| 1 | Heavy | Void | 40 | 117 |
| 1 | Heavy | Disconnect | 45 | 0 |

To generate pad cycle scenarios, a selection of variables in each pad cycle were studied; such as number of void events in each pad cycle; time between the void events, and the volume of the void events. The first step in generating the scenario for each pad cycle is to know how many void events are in that pad cycle. The number of void events in each pad cycle is computed with the probability of their occurrence in the historical data. Then for each void event, the period of time that it takes for the void event to happen and the volume of the void event are generated. The period of time and the volume are generated with their probability of occurrence in the historical data. As an example to find the probability of the void volume in each void event, we need to know the exact volume of the void event.

Since the exact volume of the void events in the historical data are unknown. One approach is to find the average voided volume of each void event in each pad cycle. This can be calculated as follows:

$$\text{Average volume}_i = \frac{\text{total volume}_i}{\text{number of events}_i}$$

Figure 13:
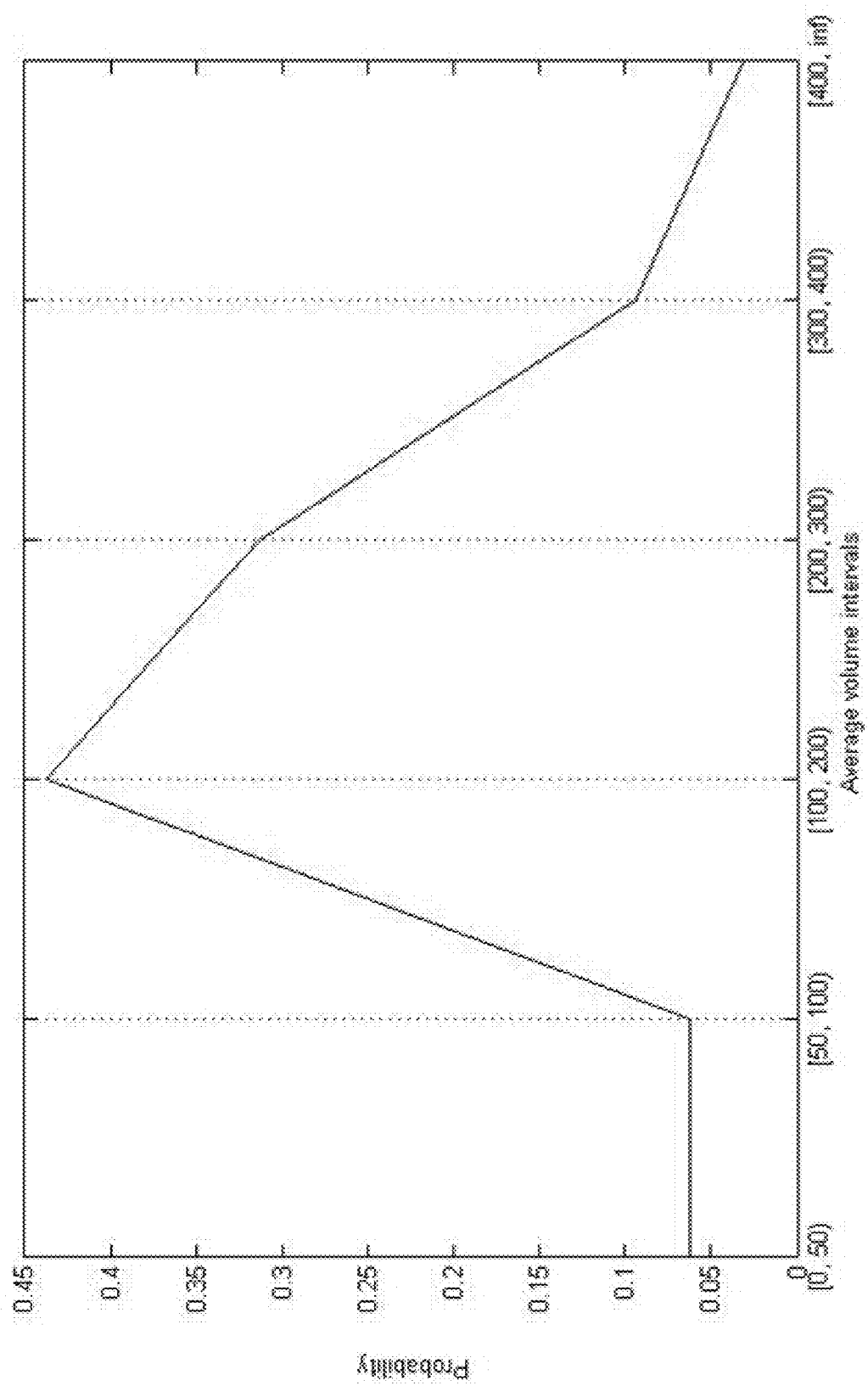
FIG. 13 shows the probability for the average volumes of each void event for the data set that were collected from a selection of aged care facilities.

Then the average volumes are categorized into some intervals, e.g. [0,50], [50,100], [100, 200], [200,300], [400, 2000]. FIG. 13 shows the probability for the average volumes of each void event for the data set that were collected from a selection of aged care facilities.

To include randomness in the void volume, after selecting the band of the volume based on the probabilities given in FIG. 13, the floor of the band (interval) is added with a random value times difference of this band, as follows:

volume=floor$_i$+(ceiling$_i$−floor$_i$)·rand( ).

Figure 14:
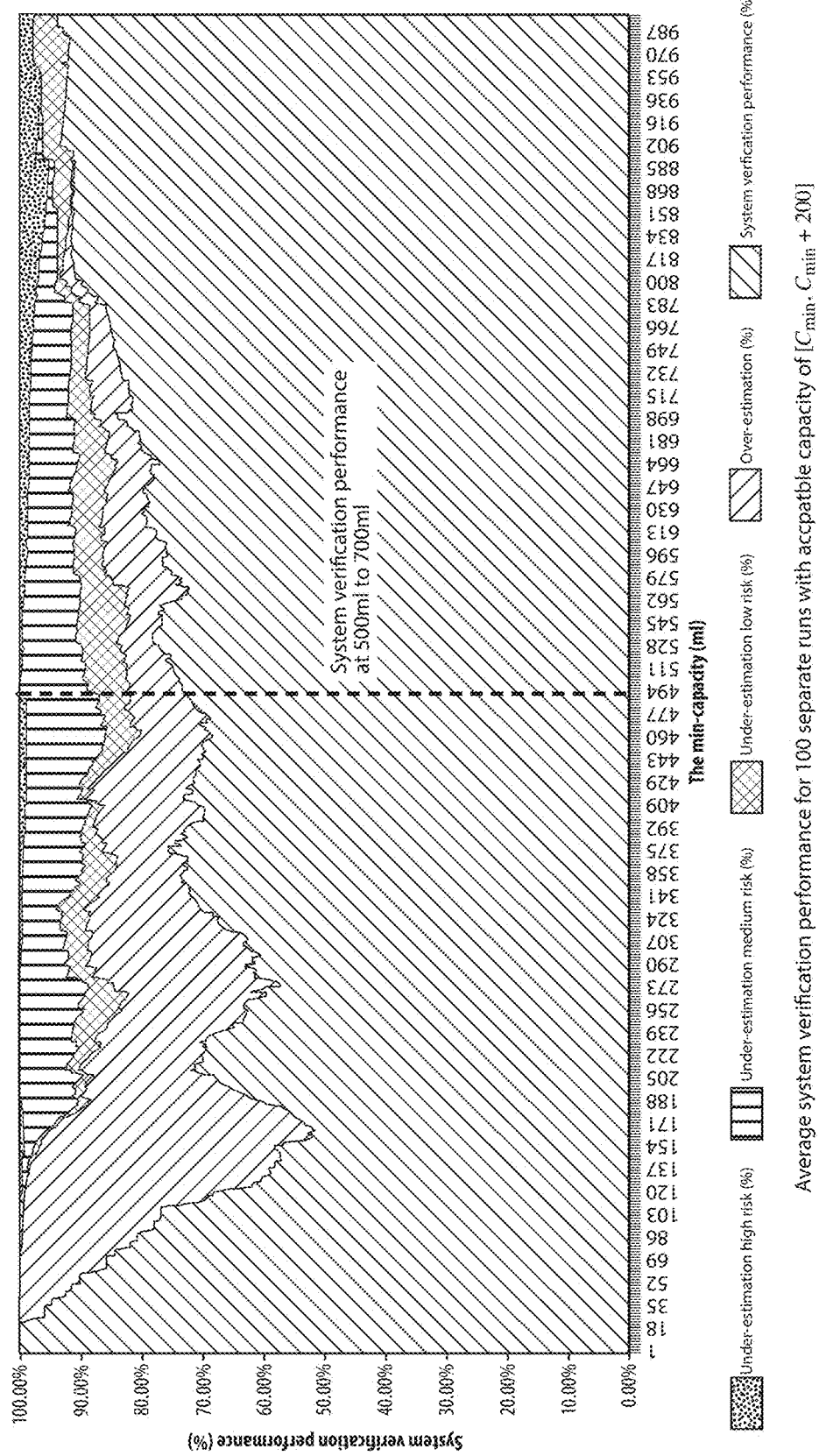
FIG. 14 illustrates average system verification performance of the method for 100 separate training and testing sets.

After simulating 119 pad cycles, the data set was randomly divided into training (90%) and testing (10%) sets. 100 separate training and testing sets were carried out. The average error of the individual and cumulative volumes over the training sets for 100 sets with random seeds are provided in Table 1. As an example, the estimated and the actual volume of the individuals of one pad cycle for the testing set for one of the 100 sets is provided in Table 2. For verification of the method, the system verification performance for min_capacity of 0 ml to 1000 ml with difference of 200 ml between min_capacity and max_capacity over the 100 testing sets are provided. This means that the max_capacity is set from 200 ml to 1200 ml. The verification in performance is shown in FIG. 14.

TABLE 1

The average error for testing and training sets with three objective functions.

| | Measurement | Training set | Testing set |
|---|---|---|---|
| 1. | Correct time to change % (500 ml-700 ml) | 73.77% | 73.21% |
| | Over-estimation % | 9.16% | 8.63% |

TABLE 1-continued

The average error for testing and training sets with three objective functions.

| | Measurement | Training set | Testing set |
|---|---|---|---|
| | Under-estimation low risk % | 6.71% | 6.99% |
| | Under-estimation medium risk % | 9.52% | 11.08% |
| | Under-estimation high risk % | 0.83% | 0.09% |
| 2. | Average error for each event (ml) | 71.3477 | 76.8516 |
| | Standard deviation of error | 54.7764 | 61.0811 |
| | Average volume of event (ml) | 192.2541 | 183.0525 |
| 3. | Ave. error for each pad cycle (ml) | 84.5675 | 113.0037 |
| | Standard deviation of error | 74.3227 | 98.7472 |
| | Average volume of pad cycle (ml) | 559.4574 | 529.4673 |

TABLE 2

An example of estimated versus actual volumes in a pad cycle.

| | Actual volume | Actual volume |
|---|---|---|
| $1^{st}$ urinary event | 92 ml | 145.30 ml |
| $2^{nd}$ urinary event | 263 ml | 160.53 ml |
| $3^{rd}$ urinary event | 60 ml | 67.73 ml |
| $4^{th}$ urinary event | 132 ml | 192.44 ml |

As an example, system validation performance of around 65% for min_capacity=200 ml and max_capacity=400 ml is desirable. The performance tends to be better with higher min_capacity and max_capacity. Also, also it has been realised that by increasing the difference between min_capacity and max_capacity, the system validation performance improves.

The above example provides a portable wireless incontinence monitoring system that alerts a caregiver only if wearer of a diaper has to be changed. For doing so, there is provided a volume estimation model which is tuned by genetic algorithms. There is also provided a time to change objective function to reflect the validation process of the system in the market. The emulation results reveal that the system has an average of 73% system verification performance for the acceptable changing volumes of between 500 ml to 700 ml. More importantly, the results indicate that in more than 89% of the cases, the system can avoid the medium or high risk scenarios of a diaper being changed after having received a total volume of greater than its maximum capacity of 700 ml.

The invention claimed is:

1. A method for determining a wetness status of an absorbent article worn by a subject, the method comprising:
   receiving sensor signals from a sensor representing one or more wetness events occurring in an absorbent article;
   processing the sensor signals to determine a cumulative volume of the pone or more wetness events, the step of processing the sensor signals comprising:
   identifying automatically the sensor signals representative of each individual wetness event and, from the sensor signals representative of each individual wetness event:
   (i) generating a representative vector for that wetness event;
   (ii) allocating weightings to the representative vector to generate a weighted representative vector for that wetness event; and
   (iii) allocating a wetness event volume to the weighted representative vector for that event; and
   determining which of one or more volume ranges contains the cumulative volume, wherein each one of the volume ranges represents the wetness status.

2. The method of claim 1, wherein the wetness status includes whether it is the correct time to change the absorbent article worn by the subject.

3. The method of claim 1, wherein determining which of one or more volume ranges contains the cumulative volume, includes comparing the cumulative volume with:
   an upper threshold wetness volume capacity of the absorbent article; or
   a lower threshold wetness volume capacity of the absorbent article.

4. The method of claim 3, wherein the upper and lower thresholds are selected from the group including 0 ml-200 ml, 100 ml-300 ml, 200 ml-400 ml, 300 ml-500 ml, 400 ml-600 ml, 500 ml-700 ml and 600 ml-800 ml.

5. The method of claim 1, wherein allocating a wetness event volume to the weighted representative vector for that wetness event includes comparing the weighted representative vector with clusters of weighted representative vectors to determine which one or more of the clusters the weighted representative vector is most similar to and allocating a wetness event characteristic of the one or more clusters to the weighted representative vector for that wetness event, wherein the wetness event characteristic indicates wetness event volume for that wetness event.

6. The method of claim 5, wherein the wetness event characteristic allocated to the weighted representative vector is a weighted average of wetness event characteristics of more than one cluster according to a degree of similarity of the weighted representative vector to the one or more clusters.

7. The method of claim 1, including carrying out a learning phase including the steps of:
   receiving sensor signals representing one or more wetness events in each of one or more absorbent articles;
   receiving observation data indicative of a cumulative characteristic of the one or more wetness events in each absorbent article;
   identifying an optimal mathematical model describing a relationship between the sensor signals and the observation data.

8. The method of claim 7, wherein the mathematical model includes a system of linear equations describing the relationship between the sensor signals and the observation data.

9. The method of claim 7, further including:
   (i) generating a representative vector for each individual wetness event, the representative vector being comprised of one or more elements;
   (ii) allocating weightings to the elements of the representative vector to generate a weighted representative vector;
   (iii) allocating each of the weighted representative vectors to one or more of a plurality of clusters of weighted representative vectors according to their relative similarity; and
   (iv) allocating a wetness event volume to each of the clusters based on the optimal mathematical model obtained during the learning phase.

10. The method of claim 9, further including normalizing the elements of the representative vector with respect to a reference range and allocating the weightings to the normalized elements of the representative vector to generate a weighted normalized representative vector.

11. The method of claim 9, further including categorizing the representative vectors of events according to order of occurrence in a sequence of events in the absorbent article and allocating different weightings to elements of the representative vectors according to their category.

12. The method of claim 9, wherein the elements of the representative vector include one or more values derived from the sensor signals.

13. The method of claim 9, wherein an element of the representative vector includes a value representing information from any one or more of a group of information types including:
   demographic information;
   environmental information
   the order of the event in a sequence of events for the absorbent article.

14. The method of claim 9, further including determining degree of belief of belonging information including, for each of the weighted representative vectors, determining a degree of belief of belonging to one or more of the plurality of clusters.

15. The method of claim 14, further including training a fuzzy neural network with the weighted representative vectors and the degree of belief of belonging information determined for each of the weighted representative vectors.

16. The method of claim 15, wherein training the fuzzy neural network includes the step of allocating information to each of the clusters including a void volume and a series of values corresponding to the degrees of belief of belonging information determined for each of the representative vectors.

17. The method of claim 14, further including using the trained fuzzy neural network during an assessment phase to determine degree of belief of belonging information for a weighted representative vector representing an event in an absorbent article including determining a degree of belief of belonging to one or more of the plurality of clusters.

18. The method of claim 7, further including verifying the correctness of the optimal mathematical model by receiving one or more sensor signals from a sensor representing an event in an absorbent article, processing the sensor signals to determine a characteristic of the event based on the optimal mathematical model obtained during the learning phase and comparing the determined characteristic with observation data.

19. The method of claim 7, identifying an optimal mathematical model includes determining a plurality of objective functions of the mathematical model and determining optimal values for the objective functions in a predetermined hierarchical order.

20. The method of claim 1, including alerting a caregiver of the absorbent article wetness status.

21. An incontinence monitoring system for determining a wetness status of an absorbent article worn by a subject, the system comprising:
   an absorbent article including a sensor for sensing wetness events occurring in the absorbent article;
   a processor for receiving sensor signals from the sensor representing one or more wetness events occurring in the absorbent article and processing the sensor signals to determine a cumulative volume of the one or more wetness events, the step of processing the sensor signals comprising:
      identifying a representative of each individual wetness event and, from the sensor signals representative of each individual wetness event:
         (i) generating a representative vector for that wetness event;
         (ii) allocating weightings to the representative vector to generate a weighted representative vector for that wetness event; and
      (iii) allocating a wetness event volume to the weighted representative vector for that event;
   determining which of one or more volume ranges contains the cumulative volume, wherein each one of the volume ranges represents the wetness status.

22. The method of claim 21, wherein the wetness status includes whether it is the correct time to change the absorbent article worn by the subject.

23. The system of claim 21, wherein determining which of one or more volume ranges contains the cumulative volume, includes comparing the cumulative volume with:
   an upper threshold wetness volume capacity of the absorbent article; or
   a lower threshold wetness volume capacity of the absorbent article.

24. The system of claim 21, wherein the processor sends information that is received by a caregiver's mobile device alerting the caregiver of the absorbent article wetness status.

* * * * *